US011185138B2

(12) United States Patent
Maltezos et al.

(10) Patent No.: US 11,185,138 B2
(45) Date of Patent: Nov. 30, 2021

(54) MANAGING OPTICAL CHARACTERISTICS OF GEMSTONES WITH DIFFRACTIVE STRUCTURES

(71) Applicant: Sparkle Cut Diamonds, Inc., St. Augustine, FL (US)

(72) Inventors: George Maltezos, Owego, NY (US); Mark L. de Naray, St. Augustine, FL (US)

(73) Assignee: SPARKLE CUT DIAMONDS, INC., St. Augustine, FL (US)

( * ) Notice: Subject to any disclaimer, the term of this patent is extended or adjusted under 35 U.S.C. 154(b) by 474 days.

(21) Appl. No.: 16/053,524

(22) Filed: Aug. 2, 2018

(65) Prior Publication Data
US 2019/0037980 A1    Feb. 7, 2019

Related U.S. Application Data

(60) Provisional application No. 62/540,844, filed on Aug. 3, 2017.

(51) Int. Cl.
*A44C 17/00* (2006.01)
*G01N 33/38* (2006.01)
(Continued)

(52) U.S. Cl.
CPC ......... *A44C 17/001* (2013.01); *G01N 33/381* (2013.01); *G06F 30/20* (2020.01); *G01N 21/87* (2013.01)

(58) Field of Classification Search
CPC ..... G06F 30/20; A44C 17/001; A44C 17/002; G01N 33/381
See application file for complete search history.

(56) References Cited

U.S. PATENT DOCUMENTS 3,808,836 A * 5/1974 Jones .................. A44C 17/003
63/32
5,966,673 A * 10/1999 Shannon, Sr. ......... G01N 21/87
356/30

(Continued)

FOREIGN PATENT DOCUMENTS

WO    WO 2018/067022    4/2018

OTHER PUBLICATIONS

Vladimír Smutný,"Light Propagation in Transparent Polyhedra", PhD Thesis CTU-CMP-2014-11, Aug. 2014 (Year: 2014).*
(Continued)

*Primary Examiner* — Kamini S Shah
*Assistant Examiner* — Russ Guill
(74) *Attorney, Agent, or Firm* — Minta Law Group LC; Veronica-Adele Dela Roca Cao

(57) ABSTRACT

Methods, apparatus, and systems for managing optical characteristics of gemstones with diffractive structures are provided. In one aspect, a method includes obtaining a three-dimensional model of a gemstone including representations of surfaces of the gemstone, identifying a region on a surface of the gemstone having an optical value higher than one or more other regions on the surface of the gemstone by analyzing the three-dimensional model of the gemstone, and determining a diffractive structure to be arranged on the identified region of the surface of the gemstone, such that the gemstone with the diffractive structure has a higher optical performance than the gemstone without the diffractive structure. The method can also include fabricating the determined diffractive structure on the identified region of the surface of the gemstone.

18 Claims, 32 Drawing Sheets

(51) Int. Cl.
*G06F 30/20* (2020.01)
*G01N 21/87* (2006.01)

(56) References Cited

U.S. PATENT DOCUMENTS

| | | | | |
|---|---|---|---|---|
| 6,187,213 | B1 | 2/2001 | Smith et al. | |
| 8,033,136 | B2* | 10/2011 | Maltezos | A44C 17/001 |
| | | | | 63/32 |
| 8,233,218 | B1 | 7/2012 | Mossberg et al. | |
| 8,314,989 | B1* | 11/2012 | Mossberg | G02B 5/1819 |
| | | | | 359/567 |
| 8,479,538 | B2* | 7/2013 | Maltezos | A44C 17/00 |
| | | | | 63/32 |
| 9,292,966 | B2* | 3/2016 | Sivovolenko | G01N 21/87 |
| 2006/0074588 | A1* | 4/2006 | Blodgett | A44C 17/001 |
| | | | | 702/179 |
| 2014/0063485 | A1* | 3/2014 | Palmieri | G01N 21/87 |
| | | | | 356/30 |
| 2014/0075991 | A1 | 3/2014 | He | |
| 2014/0107986 | A1 | 4/2014 | Sivovolenko | |
| 2014/0139608 | A1* | 5/2014 | Rosario | B23K 26/359 |
| | | | | 347/225 |
| 2015/0101365 | A1 | 4/2015 | Hui et al. | |

OTHER PUBLICATIONS

Al Gilbertson et al., Cutting Diffraction Gratings to Improve Dispersion ('Fire') in Diamonds, Gems & Gemology, Winter 2009 (Year: 2009).*

Jose Sasian et al., "Evaluation of brilliance, fire, and scintillation in round brilliant gemstones," 2007, Optical Engineering, vol. 46, issue 9, 25 pages (Year: 2007).*
Ilene M. Reinitz et al., "Modeling the appearance of the round brilliant cut diamond: an analysis of fire, and more about brilliance," 2001, Gems & Gemology, vol. 37, No. 3, 24 pages (Year: 2001).*
Jose M. Saisian et al., "The optical design of gemstones," Apr. 2003, Optics and Photonics News, 6 pages (Year: 2003).*
Nahum Stern, "Computer ray tracing in faceted gemstones," 1975, The Weizmann Institute of Science, 96 pages (Year: 1975).*
U.S. Appl. No. 62/540,844, filed Aug. 3, 2017, Maltezos et al.
Babinec et al., "Design and focused ion beam fabrication of single crystal diamond nanobeam cavities," Journal of Vacuum Science & Technology B, Nanotechnology and Microelectronics: Materials, Processing, Measurement, and Phenomena 29(1):010601, Jan. 10, 2011.
Xu et al., "Fabrication of micro DOE using micro tools shaped with focused ion beam." Optics express 18(8):8025-8032, Apr. 12, 2010.
Zinoviev et al., "Diffraction grating couplers milled in Si 3 N 4 rib waveguides with a focused ion beam," Optics express 13(21):8618-8624, Oct. 17, 2005.
[online] Smutny, "Light propagation in transparent polyhedral," Retrieved from the Internet on Nov. 25, 2016: URL:ftp://cmp.felk.cvut.cz/pub/cmp/articles/smutny/Smutny-TR-2014-11.pdf dated Aug. 31, 2014, 135 pages.
International Search Report and Written Opinion in Application No. PCT/US2018/045020, dated Jan. 16, 2019, 18 pages.
International Preliminary Report on Patentability in Application No. PCT/US2018/045020, dated Feb. 4, 2020, 11 pages.
Catalan, Ernesto Vargas, "Microfabrication of Optical Components in Synthetic Diamond Infrared Optics for Applications in Astronomy and Spectroscopy," Doctoral Dissertation, Acta Universitatis Upsaliensis, 2018.

* cited by examiner

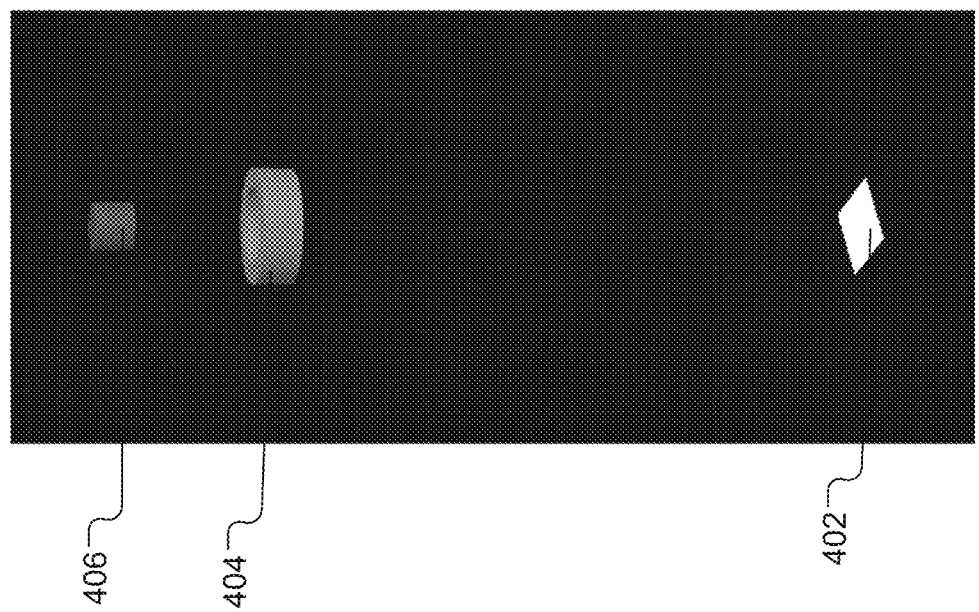

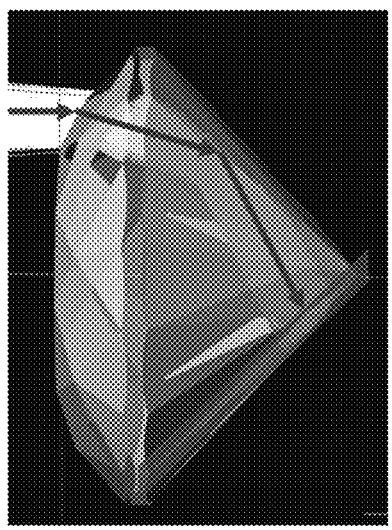
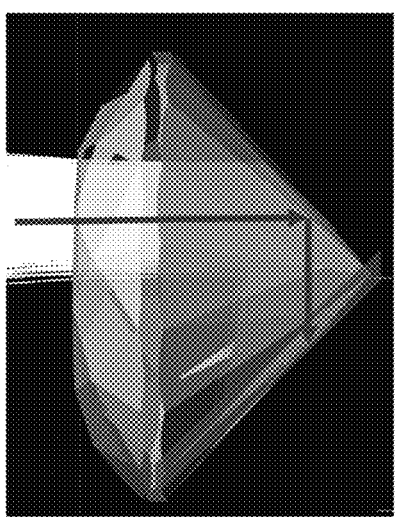
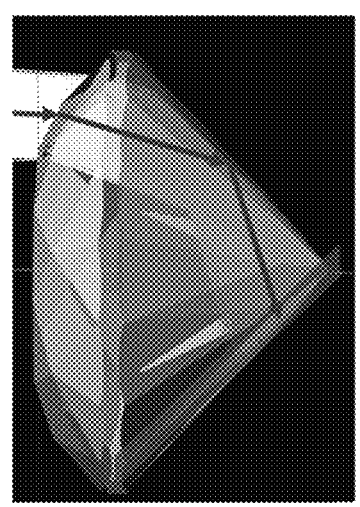
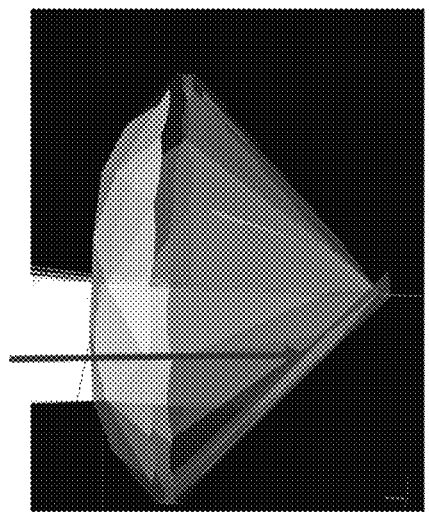
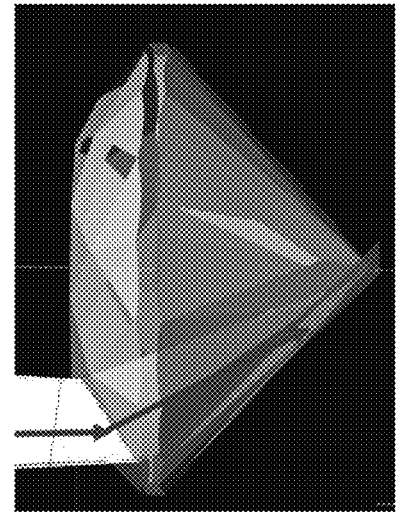
A1  A2  A3  A4  A5
FIG. 5A

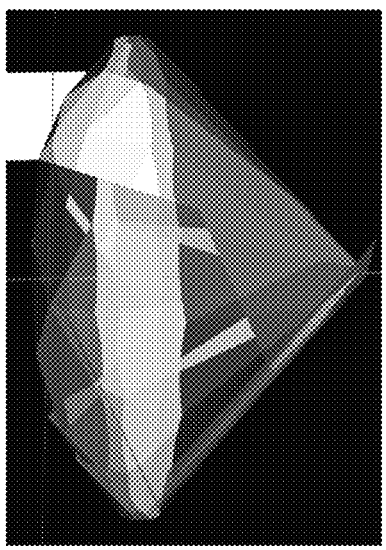
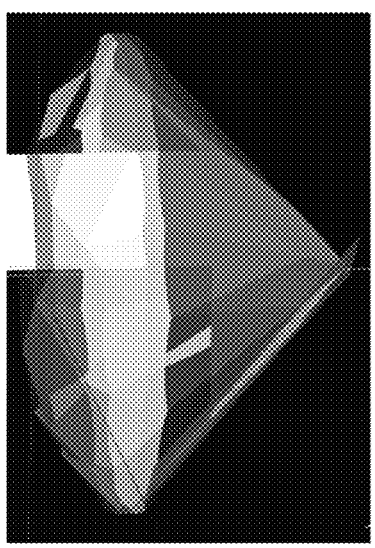
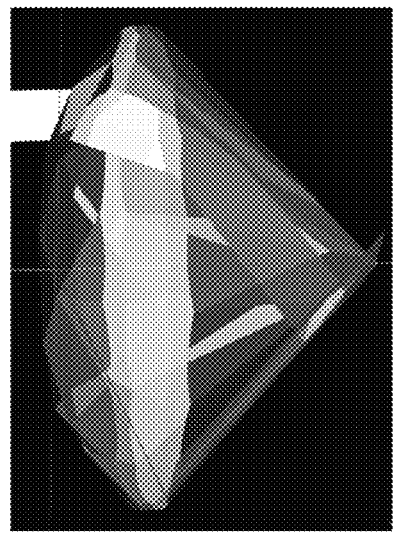
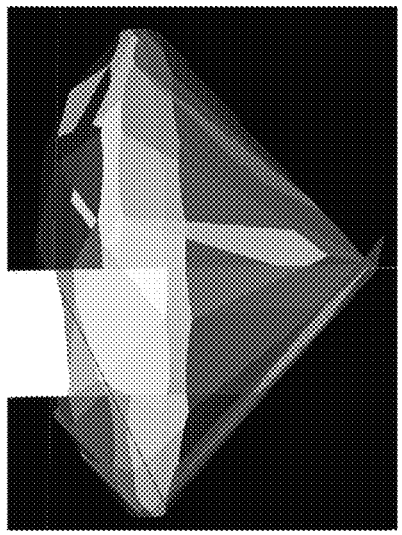
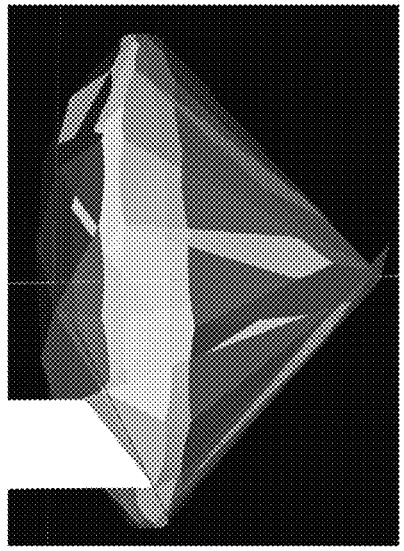
FIG. 5B

1918

1952 — Select a diamond to be processed

1954 — Select a facet of the diamond

1956 — Align the facet

1958 — Identify a region on the facet

1960 — Write a diffractive structure on the identified region

1962 — Complete processing the selected diamond

FIG. 19B

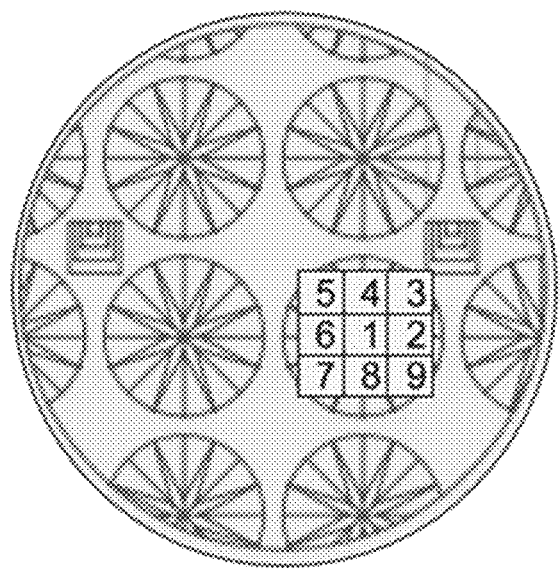
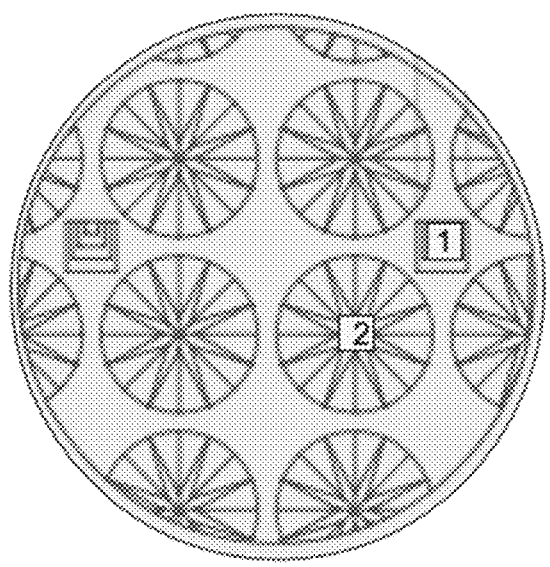
FIG. 20C
FIG. 20D

MANAGING OPTICAL CHARACTERISTICS OF GEMSTONES WITH DIFFRACTIVE STRUCTURES

CROSS-REFERENCE TO RELATED APPLICATION

This application claims priority under 35 USC § 119(e) to U.S. Provisional Patent Application Ser. No. 62/540,844, filed on Aug. 3, 2017, the entire content of which is hereby incorporated by reference.

TECHNICAL FIELD

This specification relates to gemstones and jewelry, and more particularly to managing optical characteristics of gemstones or jewelry with diffractive structures.

BACKGROUND

Gemstones are prized for their rarity and beauty. Among gemstones, particularly diamonds, are highly valued. When used for their aesthetic quality, diamond crystals are often cut and polished in ways that emphasize certain optical properties, e.g., brilliance or fire. Some methods have been developed to put diffraction gratings on diamonds to enhance their optical properties such as fire. However, as the diamonds are generally handmade, e.g., from natural stones, and can have vastly different optical qualities, it is difficult for the methods to be consistent on light performance improvement. And it is also costly to use the methods to manufacture the diffraction gratings on the diamonds.

SUMMARY

The present specification describes methods, apparatus, and systems for managing optical characteristics (e.g., brilliance, fire, color, and/or sparkle) of gemstones (e.g., diamonds) with diffractive structures (e.g., diffraction gratings), which can achieve consistent performance improvement of the gemstones with low manufacture cost, for example, by effectively and efficiently identifying areas with high optical values on surfaces of the gemstones and fabricating suitable diffractive structures on the identified areas.

One aspect of the present specification features a method of managing optical characteristics of a gemstone with diffractive structures. The method includes: obtaining, by one or more processors, a three-dimensional model of the gemstone including representations of surfaces of the gemstone; identifying, by the one or more processors, a region on a surface of the gemstone having an optical value higher than one or more other regions on the surface of the gemstone by analyzing the three-dimensional model of the gemstone; and determining, by the one or more processors, a diffractive structure to be arranged on the identified region of the surface of the gemstone, such that the gemstone with the diffractive structure has a higher optical performance than the gemstone without the diffractive structure. The identified region can have a size substantially the same as each of the one or more other regions on the surface. The three-dimensional model can also include representations of internal structures of the gemstone.

In some cases, obtaining the three-dimensional model of the gemstone includes receiving a digital file including information of the three-dimensional model of the gemstone. In some cases, obtaining the three-dimensional model of the gemstone includes generating the three-dimensional model of the gemstone by scanning the gemstone in three dimensions, and storing information of the three-dimensional model of the gemstone in a digital file.

In some implementations, analyzing the three-dimensional model of the gemstone includes: simulating propagation of an incident light through the gemstone and reflected by the surface; and generating irradiance data representing light reflection distribution of the light on the surface. Simulating the propagation of the incident light can include tracking, by using an algorithm, the light from a virtual light source to a virtual camera via one or more optical paths in the gemstone and internally reflected by the surface in the gemstone, the irradiance data being detected on the virtual camera.

In some examples, the gemstone is a diamond having a crown and a table, and the surface is a pavilion lower main facet, and the light propagates along the optical paths through at least one of a crown or a table of the diamond.

In some implementations, identifying the region on the surface of the gemstone includes: determining the region based on the generated irradiance data representing the light reflection distribution on the surface, the optical value being defined as a ratio of an energy enclosed in the region and a total energy enclosed in the surface in the irradiance data. In some cases, the method includes determining that the optical value of the region on the surface of the gemstone is no smaller than a predetermined threshold. The predetermined threshold can be determined based on one or more properties of the gemstone. In some cases, the method includes determining that a total energy enclosed in the surface of the gemstone is no smaller than a predetermined threshold.

A maximum irradiance of the surface can be at a center of the region. In some examples, the gemstone is a diamond having a culet and a girdle, and the surface is a pavilion lower main facet, and the center of the region is closer to the culet of the diamond than to the girdle of the diamond.

In some implementations, determining the diffractive structure to be arranged on the identified region of the surface of the gemstone includes: simulating propagation of an incident light from a virtual light source to a virtual camera through the gemstone and diffracted by the diffractive structure on the identified region of the surface via one or more optical paths; and determining data detected on the virtual camera representing optical appearance of the gemstone.

In some examples, the gemstone is a diamond having a crown and a table, and the surface is a pavilion lower main facet, and the light propagates along the optical paths and exits out of the diamond from at least one of the crown or the table, the virtual camera being arranged opposite to the crown and the table and configured to receive the exited light from the diamond.

In some implementations, the diffractive structure includes a diffraction grating configured to diffract the incident light into a reflected light with a plurality of angularly separated diffractive orders. In some examples, the incident light includes a white light, and the optical appearance includes a distribution of light with different colors.

The optical performance can include at least one of brilliance, fire, color, or sparkle. In some examples, determining the diffractive structure includes determining one or more parameters of the diffractive structure such that at least one of: the optical appearance has a higher brilliance than the gemstone without the diffractive structure, the optical appearance has more fire than the gemstone without the diffractive structure, the optical appearance has a special color with a higher brightness than other colors compared to the gemstone without the diffractive structure, or the light distribution has more sparkle than the gemstone without the diffractive structure. In some examples, the method further includes at least one of: determining an average brightness of the optical appearance to be the brilliance of the gemstone; determining an average color of the optical appearance to be the fire of the gemstone; determining a brightness of the special color of the optical appearance to the color of the gemstone; or moving the virtual light source or the virtual camera in relative to the gemstone to determine a change of the average brightness and a change of the average color of the light distribution to be the sparkle of the gemstone.

In some examples, determining the diffractive structure includes at least one of: adjusting the one or more parameters of the diffractive structure to maximize the brilliance of the gemstone, adjusting the one or more parameters of the diffractive structure to maximize the fire of the gemstone, adjusting the one or more parameters of the diffractive structure to maximize the brightness of the special color of the gemstone, or adjusting the one or more parameters of the diffractive structure to maximize the sparkle of the gemstone. Determining the diffractive structure can also include adjusting the one or more parameters of the diffractive structure to diffract a maximum amount of the light to the output surface.

The diffractive structure can include a diffraction grating, and the one or more parameters comprise a period, a depth, a width, an orientation, a shape, and a blaze angle.

In some examples, the gemstone is a diamond having a culet and a girdle, and the surface is a pavilion lower main facet extending along a direction from the culet of the diamond to the girdle of the diamond, and the diffraction grating has an orientation with an angle relative to the direction. In one example, the angle is 90 degree. In another example, the angle is 0 degree. In a further example, the angle is within a range from 0 degree to 90 degree. In another example, the angle is within a range from −90 degree to 0 degree.

In some examples, the diffractive structure includes a diffraction grating having a period in a range of about 1 nm to 10 microns. In some examples, the diffractive structure includes a diffraction grating having a depth in a range of about 1 nm to 1 micron. In some examples, the diffractive structure includes a diffraction grating configured to totally reflect light from the surface arranged with the diffraction grating.

The method can further include: determining, by the one or more processors, that the optical value of the region on the surface of the gemstone is no smaller than a predetermined threshold. The method can also include: determining not to arrange a diffractive structure on a second surface opposite to the surface.

In some implementations, the method includes: identifying, by the one or more processors, a second region on a second surface of the gemstone having an optical value higher than one or more other regions on the second surface of the gemstone by analyzing the three-dimensional model of the gemstone. In some examples, the gemstone is a diamond, and the surface is a first pavilion lower main facet, and the second surface is a second pavilion lower main facet. The diamond includes a third pavilion lower main facet opposite to the first pavilion lower main facet and different from the second pavilion lower main facet, and the method can further includes determining not to arrange a diffractive structure on the third pavilion lower main facet. In some cases, the method further include: determining, by the one or more processors, a second diffractive structure to be arranged on the identified second region of the second surface of the gemstone, such that the gemstone with the diffractive structure and the second diffractive structure has a higher optical performance than without the diffractive structure and the second diffractive structure.

In some cases, the method includes determining that the optical value of the second region on the second surface of the gemstone is no smaller than a predetermined threshold. In some cases, the method includes: determining that the optical value of the second region on the second surface of the gemstone is smaller than a predetermined threshold, and in response, determining not to arrange a diffractive structure on the second surface of the gemstone.

In some cases, the method further includes: determining, by the one or more processors, a second diffractive structure to be arranged on a region of a surface of a second gemstone. The second diffractive structure of the second gemstone is different from the diffractive structure of the gemstone, such that the gemstone fabricated with the determined diffractive structure is identifiable from the second gemstone fabricated with the determined second diffractive structure.

In some cases, the method further includes: identifying, by the one or more processors, a region on a surface of a second gemstone having an optical value higher than one or more other regions on the surface of the second gemstone by analyzing a three-dimensional model of the second gemstone; and determining that the optical value of the identified region on the surface of the second gemstone is smaller than a predetermined threshold, and in response, determining not to arrange a diffractive structure on the surface of the second gemstone.

In some implementations, the method further includes: fabricating, by a fabrication machine, the determined diffractive structure on the identified region of the surface of the gemstone. The method can further include: aligning the gemstone with respect to a fabrication machine, such that the fabrication machine fabricates the determined diffractive structure on the identified region of the surface of the gemstone.

In some examples, the method further includes taking digital photographs of the surfaces of the gemstone. Aligning the gemstone can include aligning the gemstone with respect to the fabrication machine based on the digital photographs.

Aligning the gemstone can further includes: mapping the digital photographs with the three-dimensional model of the gemstone, such that the identified region of the surface of the gemstone is matched with a place where the fabrication machine is to fabricate the diffractive structure. In some cases, mapping the digital photographs with the three-dimensional model of the gemstone includes: processing the digital photographs to determine an orientation of the gemstone; and matching the orientation of the gemstone to the representations of the surfaces in the three-dimensional model of the gemstone.

Fabricating the determined diffractive structure can include: receiving, by the fabrication machine, information of the determined diffractive structure from the one or more processors; and fabricating, by the fabrication machine, the diffractive structure on the identified region of the surface of the gemstone based on the received information and the alignment of the gemstone in the fabrication machine. The fabrication machine can include a focused-ion-beam (FIB) machine or a carbon milling machine. The method can further include: aligning the gemstone with respect to the fabrication machine, such that the fabrication machine fabricates a second diffractive structure on a second identified region of a second surface of the gemstone.

In some implementations, the method further includes: measuring an optical performance of the gemstone with the fabricated diffractive structure on the identified region of the surface of the gemstone. The method can further include: adjusting, by the one or more processors and based on a result of the measurement, one or more parameters of the diffractive structure to enhance the optical performance of the gemstone. The method can also include: adjusting, by the one or more processors and based on a result of the measurement, one or more parameters of a diffractive structure to be arranged on a second surface of the gemstone.

In some cases, the method further include: fabricating one or more diffractive structures on one or more surfaces of the gemstone; measuring an optical performance of the gemstone with the fabricated diffractive structures on the surfaces; and selecting, based on a result of the measurement, a different combination of surfaces of a second gemstone to be arranged with diffractive structures.

Another aspect of the present specification features a method of fabricating diffractive structures on a gemstone, including: identifying a region on a surface of the gemstone having an optical value higher than one or more other regions on the surface of the gemstone by simulating light propagation in a digital three-dimensional model of the gemstone; determining a diffractive structure to be arranged on the identified region of the surface of the gemstone; aligning the gemstone with respect to a fabrication machine; and fabricating the determined diffractive structure on the identified region of the surface of the gemstone based on information of the determined diffractive structure and the alignment of the gemstone.

A third aspect of the present specification features a method of fabricating diffractive structures on a gemstone, including: obtaining a three-dimensional model of the gemstone; aligning the gemstone with respect to a fabrication machine based on the obtained three-dimensional model; and fabricating a diffractive structure on a surface of the gemstone based on the alignment of the gemstone.

A fourth aspect of the present specification features a method of managing optical characteristics of a gemstone with diffractive structures, including: obtaining a three-dimensional model of the gemstone including representations of a plurality of pairs of surfaces of the gemstone, each pair including two surfaces opposite to each other in a planar view of the three-dimensional model; selecting one surface from a pair of surfaces to be arranged a diffractive structure, the other surface of the pair of surfaces being left blank without arranging a diffractive structure; identifying a region on the selected surface having an optical value higher than one or more other regions on the selected surface by analyzing the three-dimensional model of the gemstone; and determining a respective diffractive structure to be arranged on the identified region, such that the gemstone with the respective diffractive structure has a higher optical performance than without the diffractive structure.

The method can further include selecting one surface from each pair of the plurality of pairs of surfaces. The surfaces can be selected from the plurality of pairs of surfaces such that the selected surfaces are evenly distributed around the gemstone.

A fifth aspect of the present specification features a method of managing optical properties of a gemstone with a diffractive structure. The method includes the following steps. First, the gemstone is scanned to create a three-dimensional (3D) solid model of the gemstone, for example, by using a scanning machine such as a 3D scanner, a camera system, a dimension HD (high definition) system or a Diascan S+ system. The 3D model can be a computer file, e.g., STL (STereoLithography) file, which can include representations for surfaces and/or internal structures. Second, the solid model is analyzed to identify locations with high optical values, for example, by a light simulation software. The optical value can be defined as light contribution of the locations to an overall appearance of the gemstone. Then the software can assign diffractive structures, e.g., diffraction gratings, to the identified locations. The diffractive structures are configured by the software to direct a maximum amount of light, e.g., brilliance, to a viewer, e.g., by designing a period, a width, a depth, an orientation, a blaze angle, or any combination thereof. That is, the diffractive structures can be used for beam steering to steer as much of an input light to a desired outgoing direction. The diffractive structures can also be configured to enhance the fire of the gemstone, a special color of the gemstone, the sparkle of the gemstone, and/or the total light return (brilliance) of the gemstone. Third, the gemstone is then fixed in a known position and digitally photographed and placed into a fabrication machine, e.g., a focused-ion-beam (FIB) machine, to be patterned. Fourth, the digital photograph is processed to determine a mapping of the 3D solid model and areas of high optical value, that is, to match the areas of high optical values to where the fabrication machine writes. Fifth, the mapping information is then fed into the fabrication machine so that the previously optimized pattern of the diffractive structures can be written on the appropriate locations of the gemstone.

A sixth aspect of the present specification features a system, including: one or more processors; and a non-transitory computer readable storage medium in communication with the one or more processors and storing instructions executable by the one or more processors and upon such execution cause the one or more processors to perform any one of the methods presented above.

A seventh aspect of the present specification features a non-transitory computer readable storage medium storing instructions executable by one or more processors and upon such execution cause the one or more processors to perform any one of the methods presented above.

Particular embodiments of the subject matter described in this specification can be implemented so as to realize one or more of the following advantages. First, the technologies described herein can use a three-dimensional model of a gemstone to identify areas with high optical values on surfaces of the gemstone and to orchestrate the diffractive structures on the identified areas. Second, the technologies can optimize diffractive structures for any diamond, e.g., hand-cut or semi-automated cut, in an automated fashion, which makes it able to deal with natural variations of diamonds. Third, the technologies can make use of the beam steering effects, diffractive effects, and/or dispersive effects of the diffractive structures to significantly increase light performance, e.g., brilliance, fire, color, and/or sparkle, of gemstones, and consistency of improved light performance. Fourth, the technologies can put a unique mark on every gemstone that can make them identifiable. For example, a fabrication machine can be controlled not to write the exact same diffractive pattern twice, that is, to write different patterns, on different gemstones, thus uniquely identifying them. Fifth, the technologies can minimize patterned areas for maximum optical performance, which enables to lower the manufacturing cost of improving a diamond's light performance to a higher level and provide higher retail value for sellers as well as a higher customer value in the market. Sixth, the technologies can improve a diamond's specific light characteristics, e.g., special color, that can be important to a customer.

The details of one or more implementations of the subject matter of this specification are set forth in the accompanying drawings and associated description. Other features, aspects, and advantages of the subject matter will become apparent from the description, the drawings, and the claims.

DESCRIPTION OF DRAWINGS

FIG. 4 is a diagram showing an example configuration including a virtual light source and a virtual camera for simulating light performance of the diamond of FIG. 3A.

FIG. 5A shows example optical paths of light from the virtual light source of FIG. 4 through the diamond of FIG. 3A and reflected by the selected facet of FIG. 3B.

FIG. 5B shows example optical paths of light from the virtual camera of FIG. 4 through the diamond of FIG. 3A.

FIGS. 19A-19B are flowcharts of an example process of fabricating diffractive structures on a number of diamonds.

FIGS. 20A-20G are schematic diagrams showing steps of the example process of FIGS. 19A-19B.

DETAILED DESCRIPTION

Figure 1:
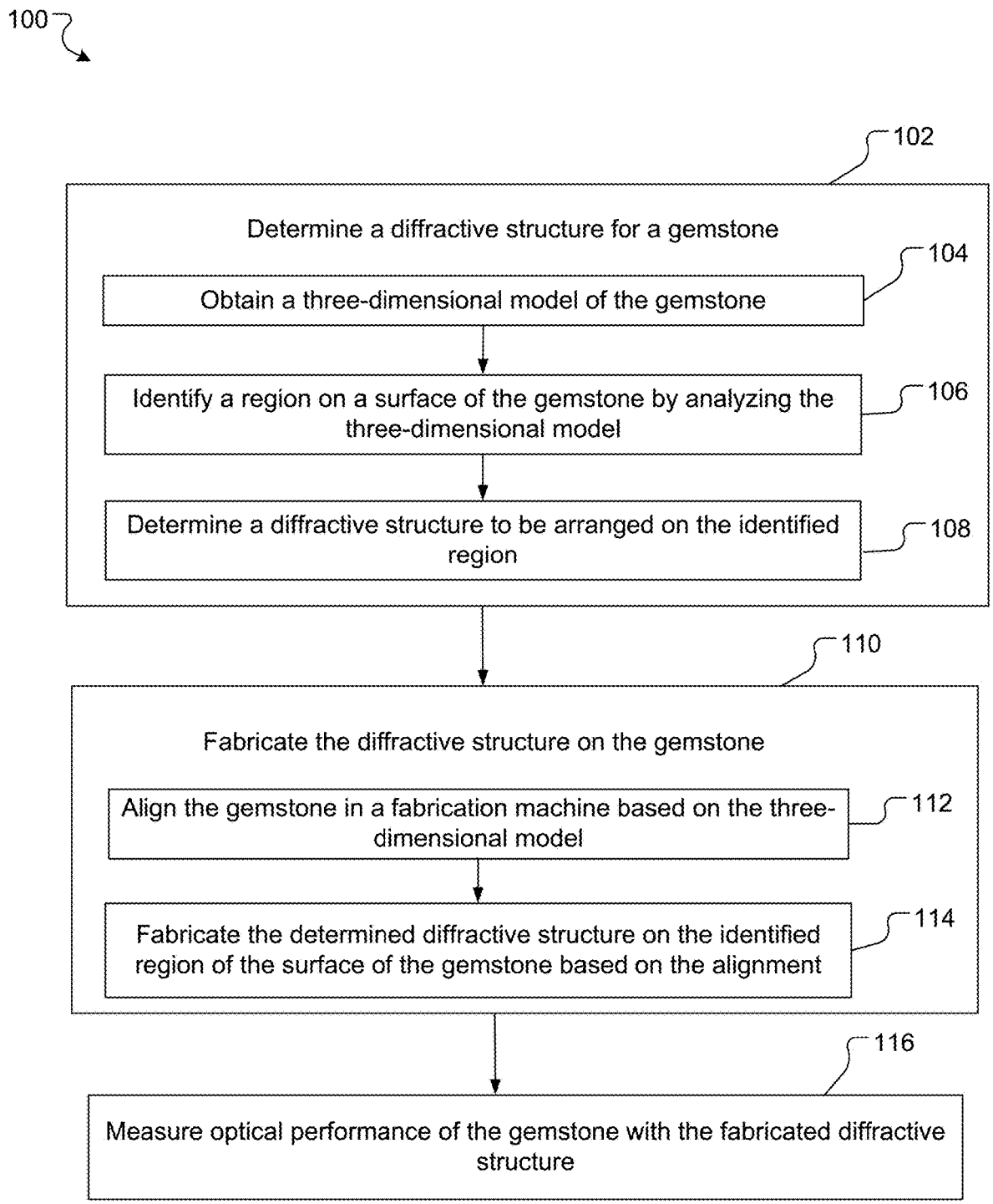
FIG. 1 is a flowchart of an example process of managing optical properties of a gemstone with diffractive structures.
Figure 2:
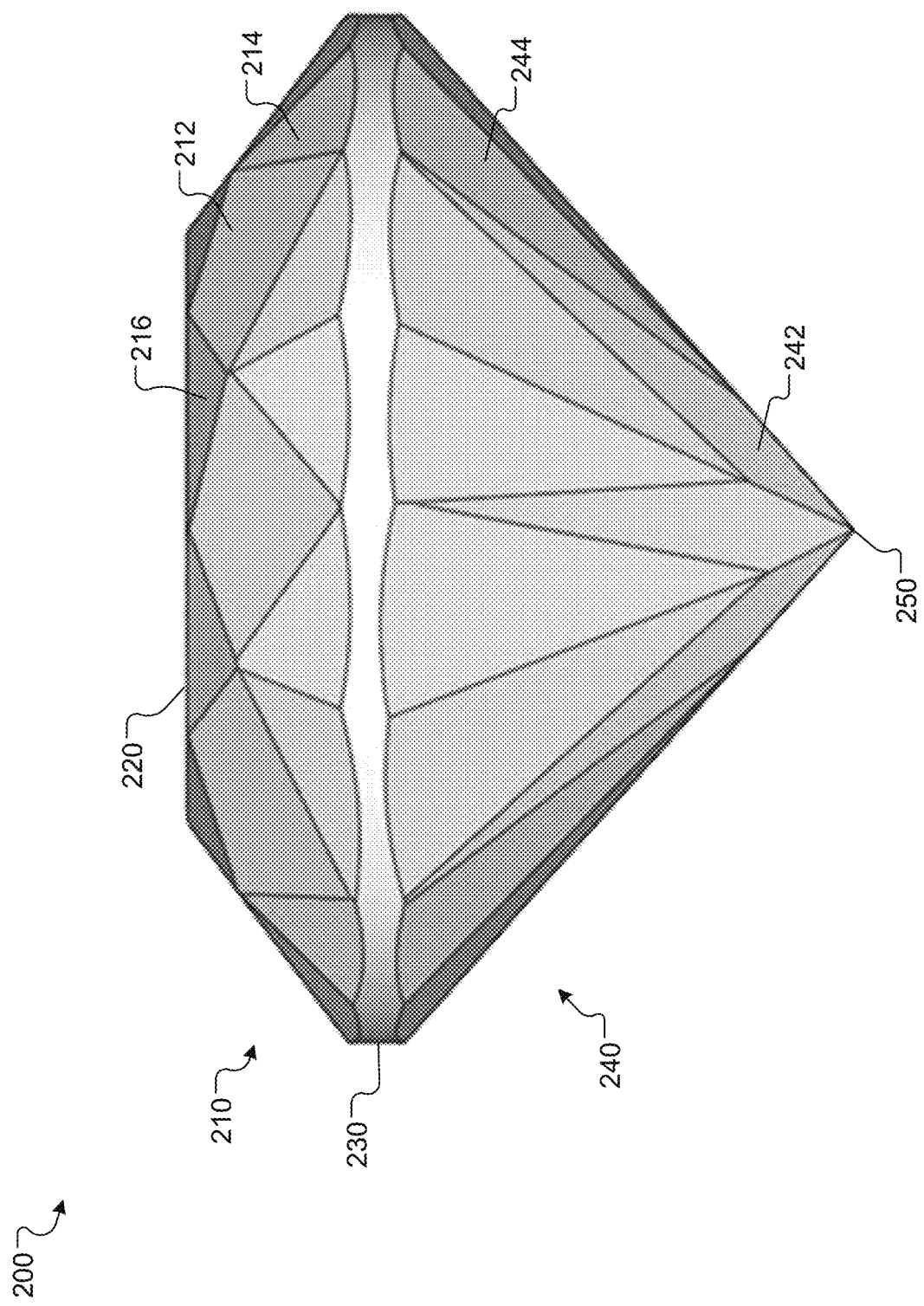
FIG. 2 is a schematic diagram of a round brilliant cut diamond as an example gemstone.

Implementations of the present specification provide methods of managing optical characteristics of a gemstone by applying diffractive structures to surfaces of the gemstone. FIG. 1 shows an example process of the methods. FIG. 2 shows a round brilliant cut diamond as an example gemstone. FIGS. 3A to 7C show example simulations for identifying a region with a high optical value on surfaces of the diamond. FIG. 8 shows a diffraction grating as an example diffractive structure. FIGS. 9A to 18B show example simulations for determining diffraction gratings to enhance optical performance of the diamond. FIGS. 19A to 20G show an example process for fabricating diffractive structures on a number of diamonds.

The methods described herein can be applied to any material whose aesthetic appearance can be enhanced by beam steering effects, diffractive effects, and/or dispersive effects of diffractive structures. For example, the methods can be applied to any suitable type of gemstone, including diamonds, synthesized diamonds or any other synthetics, natural and artificial diamond stimulants and clear stones such as cubic zirconium, zircon, moissanite, topaz, rutile, strontium titanate, spinel, yttrium aluminum garnet, strontium titanate, yttrium aluminum garnet (YAG), gadolinium gallium garnet (GGG), and glass to name only a few examples. The methods could also be applied to other items of jewelry, whether optically transmissive or not (e.g., reflective diffractive structures could be used on opaque materials). The materials can be raw or have got any suitable processing such as partially cut, well cut, poorly cut, round cut, princess-cut, octagonal step-cut, unpolished, partially polished, or polished. The materials can also have any desired shape or size. For illustration purposes only, some examples in the following description are directed to round brilliant cut diamonds.

Example Process

FIG. 1 shows an example process 100 of managing optical properties of a gemstone with diffractive structures. The process 100 includes two major steps: determining a diffractive structure for the gemstone (102) and fabricating the diffractive structure on the gemstone (110). The first major step 102 can be performed by a computing system including one or more processors. The second major step 110 can be performed by a fabrication machine and optionally in combination with the computing system. The process 100 can also optionally include a third step 116 to measure an optical performance of the gemstone after the diffractive structure is fabricated on the gemstone.

A three-dimensional (3D) model of the gemstone is obtained (104). The 3D model of the gemstone can be obtained by scanning the gemstone in three dimensions, for example, by using a scanning machine such as a 3D scanner, a camera system, a dimension HD (high definition) system, or a Diascan S+ system. Information of the 3D model can be stored as a computer file, e.g., a STereoLithography file (*.STL). The 3D model can be read, viewed, and/or edited by the computing system. As illustrated in FIG. 3A, the 3D model of the gemstone includes representations of surfaces of the gemstone and optionally additional details such as surface defects and internal structures.

In some cases, the 3D model of the gemstone is obtained by receiving a computer file from another system. The computer file includes information of the 3D model. The computer file can be generated when or after a raw gemstone is cut or polished to be the gemstone.

A region on a surface of the gemstone is identified by analyzing the three-dimensional model (106). The region can be identified by analyzing the 3D model using a light simulation algorithm to simulate light propagation through the 3D model, e.g., via optical paths of a number of light rays based on reflection, refraction, and diffraction. The light simulation algorithm can include a ray-tracing algorithm based on a geometric optical approximation of light propagation, a diffraction algorithm, a simulation of Maxwell's equations which can be performed using finite difference time-domain (FDTD) or finite element methods (FEM), or any combinations or modifications thereof. The simulation algorithm can be implemented in a software.

The identified region can have a higher optical value than one or more other regions on the surface, where the identified region has a size substantially the same as each of the other regions on the surface. The optical value can be defined as light contribution of the region on the surface to an overall appearance of the gemstone. The optical value can be considered as an optical impact value used to evaluate the light reflection contributed by the region. In some cases, as discussed with further details in FIGS. 6A-6B, analyzing the 3D model of the diamond includes simulating propagation of an incident light through the gemstone and reflected by the surface and generating an irradiance plot representing light reflection distribution of the light on the surface. That is, if there is more light hitting and being reflected by a region of the surface, there can be more energy enclosed in the region of the surface in the irradiance plot. The propagation of the light can be from a virtual light source to a virtual camera via one or more optical paths in the gemstone and internally reflected by the surface, as illustrated further in FIG. 5A or 5B. The optical value can be defined as a ratio of an energy disclosed in the region and a total energy enclosed in the surface. The identified region can have the highest ratio among the regions on the surface that have a substantially same size. A maximum irradiance on the surface can be at a center of the region.

In some examples, the optical value of the identified region on the surface is compared to a predetermined threshold. If the optical value of the identified region is smaller than the predetermined threshold, it can be determined that the surface is not good. It can be further determined not to arrange a diffractive structure on the surface. If all the surfaces of the gemstone are determined to be not good, it can be determined not to arrange any diffractive structure on the gemstone. In contrast, if the optical value of the identified region is identical to or larger than the predetermined threshold, it can be determined that the surface is good. It can be further determined to arrange a diffractive structure on the surface.

The predetermined threshold can be determined based on one or more properties of the gemstone. For example, the identified region can have a predetermined size, and the predetermined threshold can be associated with the predetermined size. In a particular example, the predetermined size is about 30% of a total size of the surface, and the predetermined threshold is about 50%.

In some implementations, a total energy enclosed in the surface in the irradiance plot is determined and compared to a threshold. As discussed with further details in FIGS. 13A, 13B and 14, if the total energy is smaller than the threshold, it can be determined that the surface is not good. It can be further determined not to arrange a diffractive structure on the surface.

A diffractive structure is determined to be arranged on the identified region of the surface of the gemstone (108), such that the gemstone with the diffractive structure has a higher optical performance than without the diffractive structure. The diffractive structure is configured to cause beam steering, diffractive or dispersion effects, or any combination thereof. The diffractive structure can include a diffraction grating. The diffraction grating can be configured to diffract the incident light into a number of angularly separated diffractive orders. If the incident light is a white light, the white light can be diffracted or dispersed into a number of different colors. The diffraction grating can be configured to diffract the light into an output light with a special color, e.g., red, blue, green, violet, or any other suitable color, which is stronger than other colors in the output light if any. The diffraction grating can also be configured to diffract the light into an output light with two or more special colors that are stronger than other colors in the output light. The diffraction grating can also be configured to have the beam steering capability. Given light incident from a particular direction, the diffraction grating is configured to direct as much of the incident light as possible to exit at specified angles. For example, when the gemstone is a round brilliant cut diamond including a crown and a table, the diffraction grating on a facet of the diamond is configured to direct as much as possible light out from the crown or the table of the diamond, such that the optical performance (or optical appearance) of the diamond with the diffraction grating can be enhanced. The beam steering capability of the diffraction grating can be controlled by adjusting one or more parameters of the diffraction grating, including a depth, a width or a width varying with distance, and an orientation.

Determining the diffractive structure can include determining one or more parameters of the diffractive structure.

For a diffraction grating, the one or more parameters can include a period, a width, a depth, an orientation, a shape, and a blazed angle. In a particular example, the diffraction grating has a period in a range of about 1 nm to 10 microns. In a particular example, the diffraction grating has a depth in a range of about 1 nm to 1 micron. In a particular example, the diffraction grating has an orientation in a range of 0 degree to 90 degree. In a particular example, the diffraction grating has an orientation in a range of −90 degree to 0 degree. Note that "in a range" herein can also include lower and upper boundary values of the range. The diffraction grating can be a periodic structure, a quasi-periodic structure, or non-periodic structure. For example, a width of the diffraction grating can be varying with distance along a direction. The diffraction grating can be a uniform structure or non-uniform structure. For example, a depth of the diffraction grating can be varying with distance along a direction.

Figure 11A:
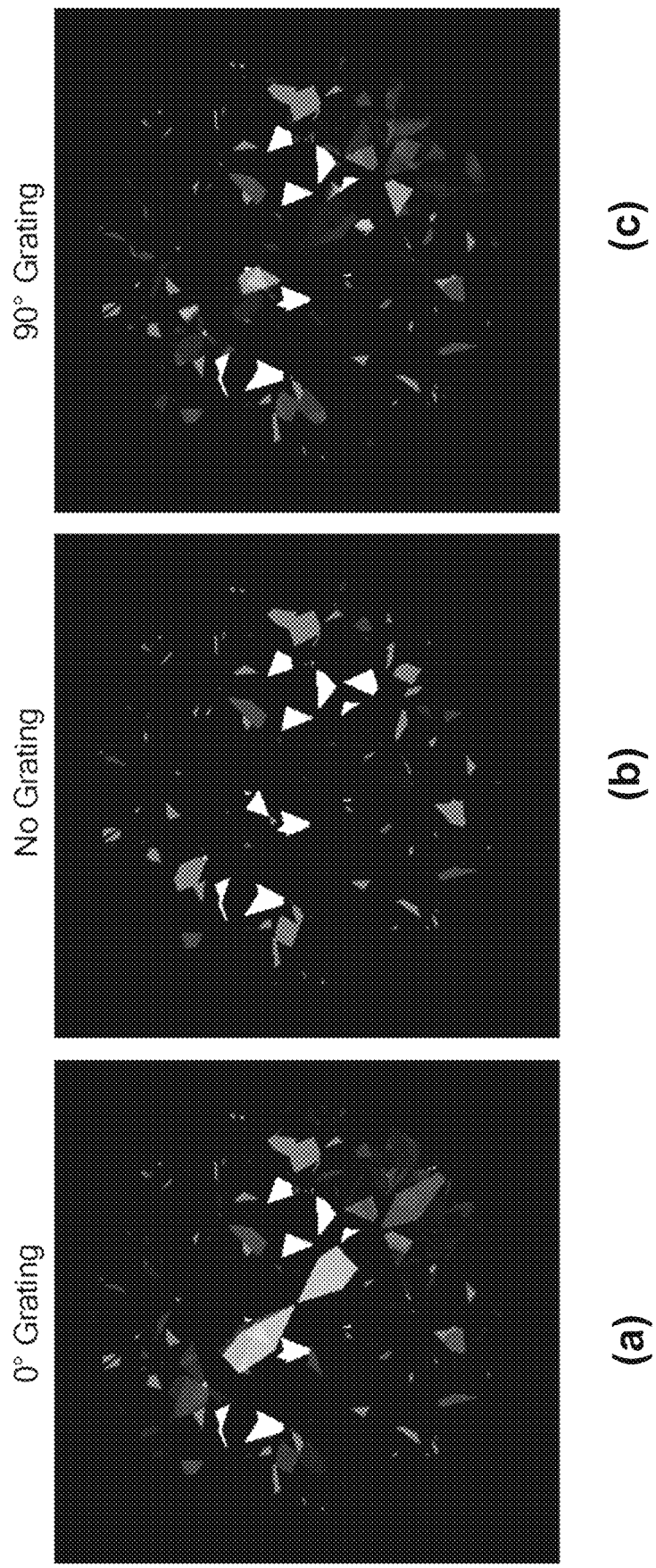
FIG. 11A shows example data detected on the virtual camera representing optical appearances of the diamond arranged with 0 degree grating (a), no grating (b), and 90 degree grating (c) on the selected facet.

The diffractive structure can be determined by simulating propagation of an incident light from a virtual light source to a virtual camera through the gemstone and diffracted by the diffractive structure on the identified region of the surface via one or more optical paths. The diffracted light can exit from the gemstone from an output surface of the gemstone. For example, a crown and a table of a diamond can be the output surface. The simulation can be performed by the light simulation algorithm mentioned above or any other algorithm that can simulate the light propagation via reflection, refraction, and diffraction or dispersion. Data representing optical appearance of the diamond can be detected on the virtual camera. The data can be a two-dimensional image, as illustrated in FIG. 11A. The data can be analyzed to generate average brightness, as illustrated as FIG. 11B, and/or average color, as illustrated in 11C.

When light enters a gemstone (e.g., a diamond), it travels through the gemstone and is reflected off or diffracted by interior surfaces (e.g., facets) of the gemstone. Then the light either leaves the diamond as a white light and/or the light divides into one or more spectral colors, e.g., red, orange, yellow, green, blue, and/or violet. The total intensity of the output light from the gemstone, including the white light and the spectral-colored light, is called brightness or brilliance. The colorfulness of the output light is called fire. A special color that is much stronger than any other colors in the output light is called color. As a viewer or the gemstone moves, an effect called scintillation occurs—visible as alternating flashes of white and spectral-colored light and the contrast of dark and light that moves around the gemstone. This contrast is dynamic and causes sparkle. The optical performance of the gemstone can include at least one of brilliance (or brightness), fire (or colorfulness), color, or sparkle.

In some cases, the optical performance includes brilliance (or brightness). The brilliance of the gemstone can be determined based on the generated data or the generated average brightness. Determining the diffractive structure can include determining the one or more parameters of the diffractive structure such that an average brightness of the optical appearance of the gemstone is larger than the gemstone without the diffractive structure. Determining the diffractive structure can also include adjusting the one or more parameters of the diffractive structure to maximize the brilliance of the gemstone, e.g., the average brightness of the gemstone.

In some cases, the optical performance includes fire (or colorfulness). The fire of the gemstone can be determined based on the generated data or the average color. Determining the diffractive structure can include determining the one or more parameters of the diffractive structure such that the optical appearance of the gemstone has more fire than the gemstone without the diffractive structure. Determining the diffractive structure can also include adjusting the one or more parameters of the diffractive structure to maximize the fire of the gemstone.

In some cases, the optical performance includes a special color. Determining the diffractive structures can include determining the one or more parameters of the diffractive structure such that the light exiting from the gemstone has the special color with the largest brightness than the other colors in the light, e.g., a dominant color. Determining the diffractive structure can also include adjusting the one or more parameters of the diffractive structure to maximize the brightness of the special color.

In some cases, the optical performance includes sparkle. The sparkle of the gemstone can be determined by moving the virtual light source or the virtual camera in relative to the gemstone and then determining a difference of the generated data before and after the moving. Determining the diffractive structure can include determining the one or more parameters of the diffractive structure such that the optical appearance of the gemstone has more sparkle than the gemstone without the diffractive structure. Determining the diffractive structure can also include adjusting the one or more parameters of the diffractive structure to maximize the sparkle of the gemstone.

In some implementations, the process 100 further includes determining a second diffractive structure for a second surface of the gemstone. Similar to step 106, a second region on the second surface of the gemstone is identified by analyzing the 3D model of the gemstone. The second region can have an optical value higher than one or more other regions on the second surface or higher than a predetermined threshold or both. The process 100 can further include determining the second diffractive structure to be arranged on the identified second region on the second surface, such that the gemstone with the diffractive structure for the surface and the second diffractive structure for the second surface has a higher optical performance than without the diffractive structures. In some cases, the second surface and the surface are adjacent. In some cases, the second surface is selected to be separated from the surface.

When a diffractive structure is arranged on a surface of the gemstone, on one side, the diffractive structure diffracts light into different directions, which may cause loss of light and reduce the brilliance of the gemstone; on the other side, the diffractive structure can perform beam steering on the light and direct the light as much as possible to a desired output surface. Moreover, when the diffractive structure is arranged on a first surface, the light can be diffracted to a second surface opposite to the first surface (or adjacent to the first surface) and reflected or bounced by the second surface, which can increase (e.g., double) the effect of the diffractive structure and also minimize the light loss. Thus, a number of factors can be considered for determining multiple diffractive structures on the gemstone, including the number of diffractive structures, the sizes of the diffractive structures, and the surfaces selected to be arranged with the diffractive structures.

In some examples, the gemstone includes a first surface and a second surface opposite to each other, e.g., in a planar view of the gemstone. If the first surface is selected to be arranged with a diffractive structure, it can be determined not to arrange a diffractive structure on the second surface.

Figure 15A:
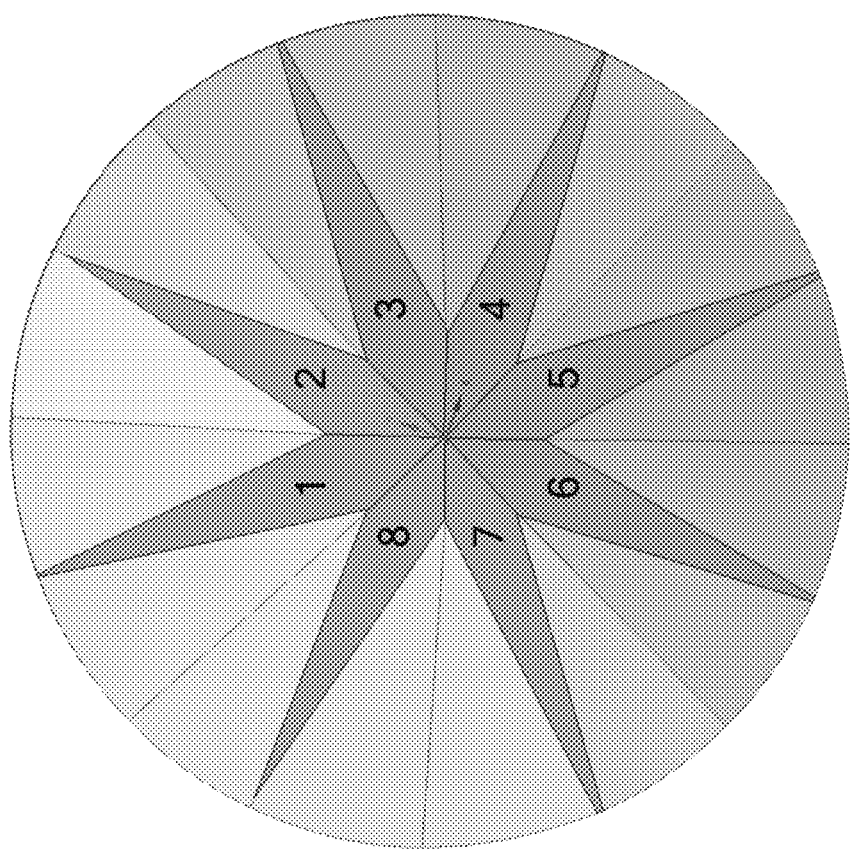
FIG. 15A shows a schematic diagram of eight lower main facets on the pavilion of FIG. 3B to be selected for diffractive structures.
Figure 16:
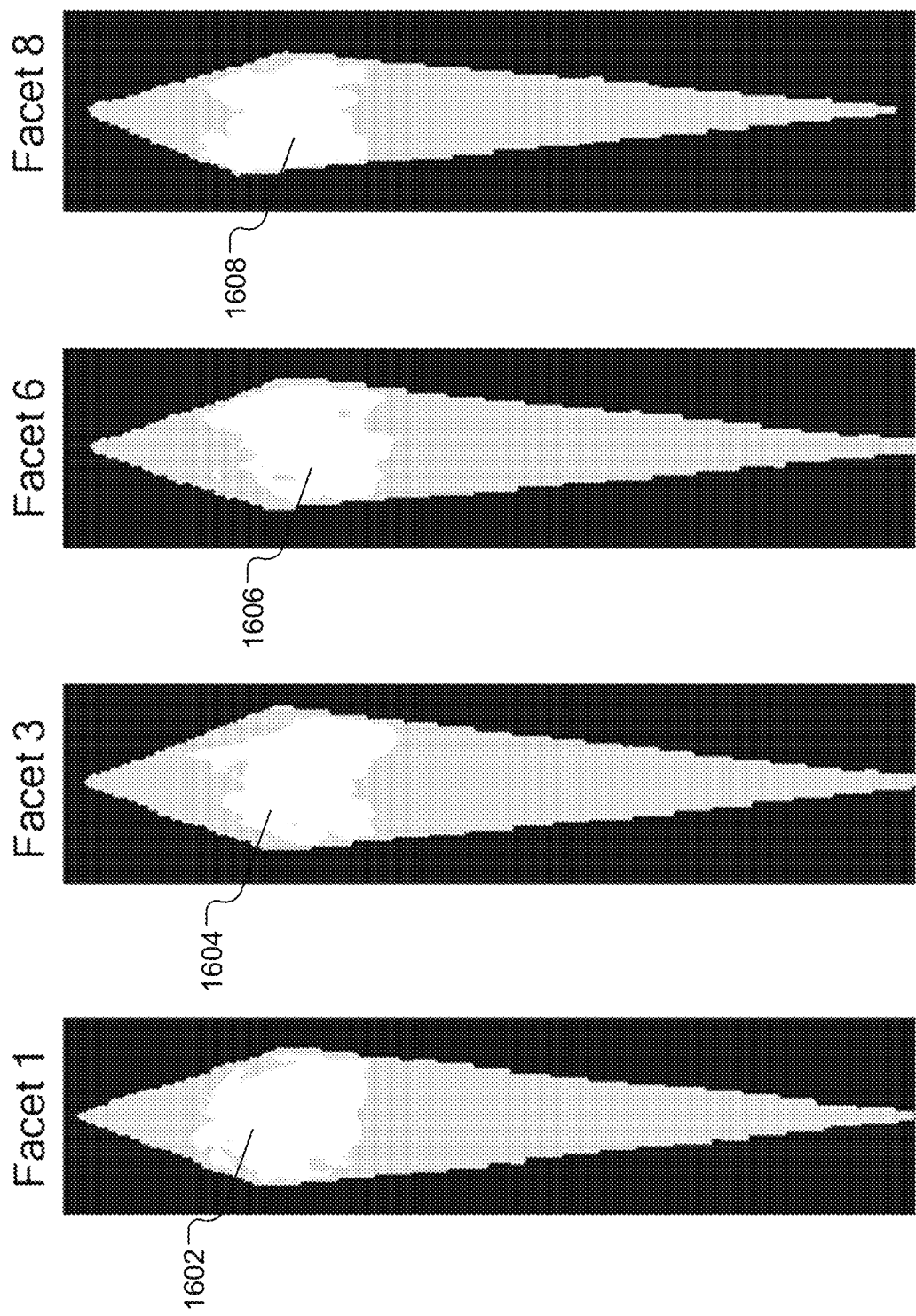
FIG. 16 show example regions with high optical values on four selected facets of FIG. 15C.

In some implementations, as illustrated in FIG. 15A, the gemstone includes a number of pairs of surfaces. In a planar view of the 3D model of the gemstone, two surfaces of each pair are opposite to each other. As illustrated in FIG. 16, one surface from each pair can be selected to be arranged with a diffractive structure, and the other surface from the same pair can be left blank without arranging a diffractive structure. In some cases, selecting one surface from each pair for the gemstone can include selecting the surfaces from the number of pairs such that light reflection by the surfaces is balanced (e.g., evenly distributed or uniform) in the gemstone, or such that the selected surfaces are evenly distributed in the gemstone. For example, as illustrated in FIG. 16, the gemstone has 4 pairs, including surfaces 1 and 5, surfaces 2 and 6, surfaces 3 and 7, and surfaces 4 and 8. The selected surfaces to be arranged with diffractive structures are surfaces 1, 3, 6, and 8. In such a way, less number of diffractive structures can be determined and fabricated on the gemstone, which can reduce cost and/or improve the optical performance of the gemstone.

Referring back to FIG. 1, after determining one or more diffractive structures on one or more surfaces of the gemstone, the process 100 proceeds to the second major step 110, that is, to fabricate the determined diffractive structures on the gemstone by the fabrication machine. The fabrication machine can include a focused-ion-beam (FIB) machine, a micro- or nano-patterning machine such as micro- or nano-lithography system, or any suitable machine or system.

In some implementations, the diffractive structures can be deposited onto the surfaces of the gemstone. The diffractive structures can include a type of material other than the gemstone (e.g., metal) upon which the structures are deposited. In some implementations, the diffractive structures can be patterned (or etched) into or on the gemstone surface itself. The diffractive structures can be located within the gemstone.

The gemstone is aligned with respect to the fabrication machine based on the 3D model of the gemstone (112), such that the fabrication machine can fabricate the determined diffractive structure on the identified region of the surface of the gemstone. As discussed with further details in FIG. 19A, the gemstone can be digitally photographed. The digital photographs can be processed, e.g., by the computing system, to determine an orientation of the gemstone and further to match or map the orientation of the gemstone with the 3D solid model and the identified region on the surface of the gemstone. The gemstone can be placed into the fabrication machine, e.g., into a chamber of the fabrication machine. The matching or mapping information can be fed into the fabrication machine. The gemstone can be aligned, e.g., by using a movable stage with an XYZ, rotation, and azimuth motion, such that the identified region on the surface is matched to where the fabrication machine writes a pattern of the diffractive structure.

The determined diffractive structure is fabricated on the identified region of the surface of the gemstone based on the alignment (114). The fabrication machine can receive information of the diffractive structure from the computing system, and fabricate the diffractive structure on the identified region of the surface of the gemstone based on the received information and the alignment. FIGS. 19A-19B and 20A-20G show an example process of fabricating the diffractive structures on the gemstone.

In some implementations, after fabricating a diffractive structure on a surface of the gemstone, the gemstone can be aligned with respect to the fabrication machine such that a second identified region on a second surface of the gemstone is matched to where the fabrication machine writes a corresponding second diffractive structure. Then, the fabrication machine fabricates the corresponding second diffractive structure on the second identified region on the second surface of the gemstone. As illustrated in FIG. 19B, the fabrication machine can perform a loop to fabricate multiple diffractive structures on multiple different surfaces on the gemstone. The fabrication machine can also continue another loop to fabricate diffractive structures on another gemstone.

In some implementations, after fabricating a diffractive structure on a surface of the gemstone (114), an optical performance of the gemstone with the fabricated diffractive structure is measured (116). The measurement can be performed by an operator using an optical device or system such as a microscope system. In some cases, based on a result of the measurement, one or more properties of the diffractive structure can be adjusted to adjust (or optimize) the optical performance of the gemstone. For example, the result of the measurement can be input into a computing system and the computing system can perform step 108 to adjust the one or more properties of the diffractive structure. The diffractive structure with the adjusted properties can be fabricated on another surface on the same gemstone or on a surface of another gemstone. In some cases, based on a result of the measurement, another diffractive structure to be arranged on a second surface of the gemstone can be re-determined or adjusted.

In some implementations, two or more diffractive structures are determined to be arranged on two or more corresponding surfaces of the gemstone. After the two or more diffractive structures are fabricated on the surfaces of the gemstone, the gemstone with the fabricated diffractive structures is measured to determine its optical performance. Based on the result of the measured optical performance, one or more properties of the diffractive structures can be adjusted or different surfaces may be selected to be arranged with diffractive structures on a gemstone.

In some implementations, different gemstones are fabricated with different diffractive structures, such that the gemstones are identifiable from each other based on the corresponding diffractive structures fabricated on them. In some cases, diffractive structures for different gemstones can be made different during the simulation, e.g., at step 108. In some cases, diffractive structures for different gemstones can be made different during the fabrication, e.g., at step 114. The fabrication machine can be controlled to modify one or more parameters of a diffractive structure to be fabricated on different gemstones.

Example Gemstone

FIG. 2 is a schematic diagram of a round brilliant cut diamond 200 as an example gemstone. An upper portion of the round brilliant cut diamond 200 is a crown 210. The crown 210 includes a flat top portion called table 220. A lower portion of the round brilliant cut is a pavilion 240, whose tip is called a culet 250. The crown 210 and the pavilion 240 are separated by a flat girdle 230 with a width to help prevent chipping that might otherwise occur if the crown 210 and pavilion 240 are joined at a sharp angle. The crown 210 includes a number of surrounding facets including upper main facets 212, upper girdle facets 214, and star facet 216. The pavilion 240 includes a number of facets including lower main facets 242 and lower girdle facets 244.

Example Simulations for Identifying Regions on Surfaces

FIG. 3A is an example three-dimensional (3D) model 300 of a round brilliant cut diamond, e.g., the diamond 200 of FIG. 2. As noted above, the 3D model 300 can include be an STL file using an 3D Cartesian (XYZ) coordinate system. Global coordinate origin (0, 0, 0) can be located at a center of a table of the diamond. The 3D model can be read, viewed, and/or edited by a computing system. The 3D model can include representations of surfaces of the diamond and optionally surface defects and internal structures.

Figure 3B:
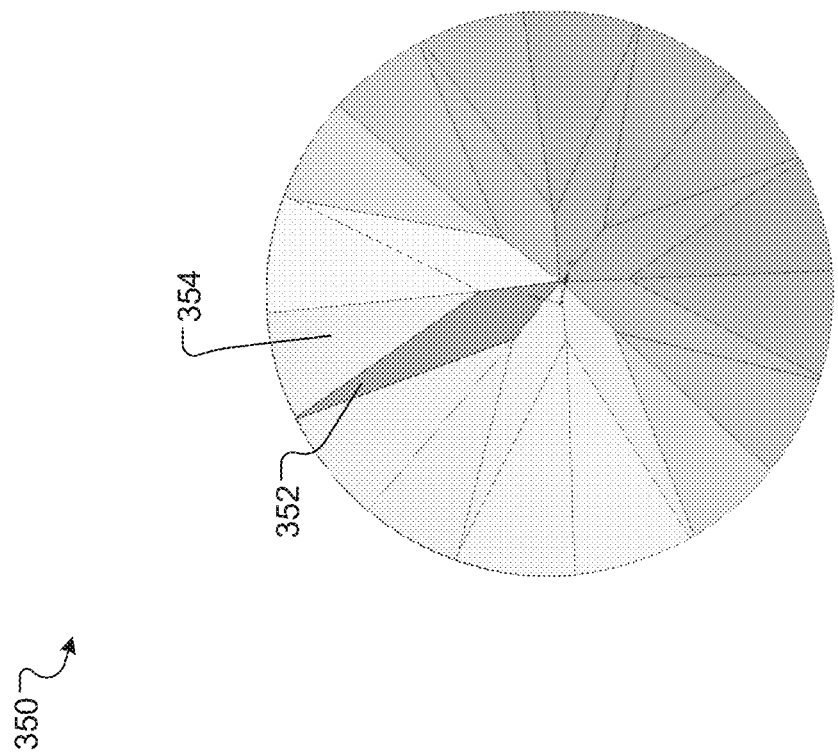
FIG. 3B is a bottom view of a pavilion of the diamond of FIG. 3A, including a lower main facet selected for consideration.
Figure 3A:
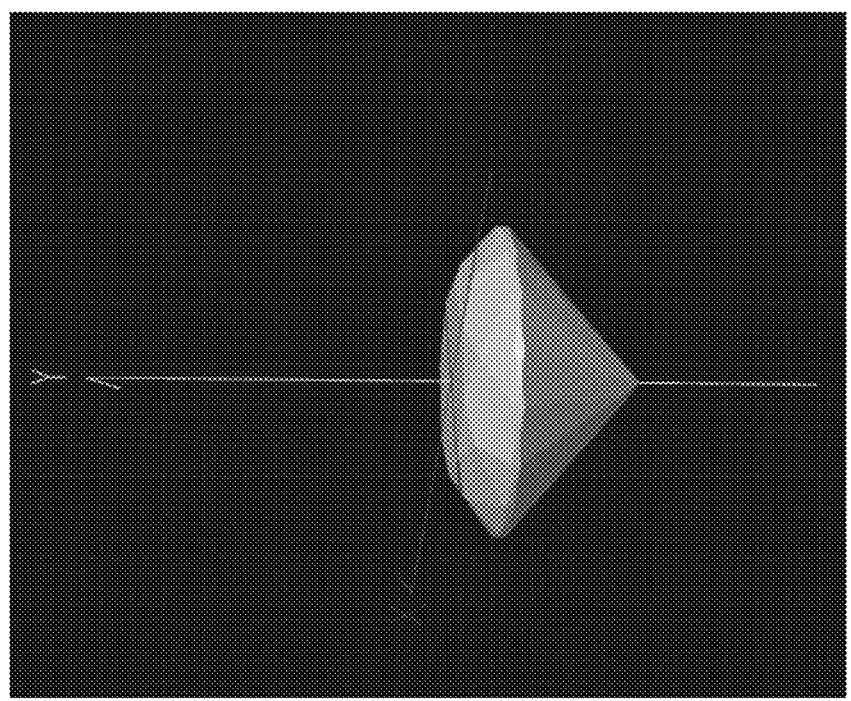
FIG. 3A is an example three-dimensional model of a round brilliant cut diamond.

FIG. 3B is a bottom view 350 of a pavilion of the diamond in the 3D model 300. The pavilion includes eight lower main facets and eight lower girdle facets. In the following simulation, a lower main facet 352 is selected for consideration. A lower girdle facet 354 is adjacent to the lower main facet 352.

FIG. 4 shows an example configuration 400 including a virtual light source 404 and a virtual camera 406 for simulating light performance of the diamond represented by FIG. 3A. The simulation can be performed by a software implementing the light simulation algorithm described above. A large white plane 402 is used to show a location of the diamond. A lower surface of a ring light as the virtual light source 404 is used as an emitting surface, which is above the diamond, e.g., about 13 inches. The ring light can have an outer diameter, e.g., 4 inches, and an inner hole, e.g., with a size of 2 inches. The virtual camera 406 has a lower surface as a collecting surface, which is above the diamond, e.g., about 14 inches.

FIG. 5A shows examples of optical paths of light from the virtual light source 404 through the diamond and reflected by the selected facet to the virtual camera 406. An optical path is one that light travels through the diamond while hitting a particular sequence of surfaces in a particular order. There can be thousands of paths which reach the selected facet, and there may be dozens with enough power to be potentially significant. Diagrams A1 to A5 show five significant paths, which can account for about 35% of the light energy reaching the selected facet. The optical paths can pass through the table or the crown of the diamond. For example, the light from the virtual light source 404 can enter into the diamond through an input surface including at least one of the table or the crown and exit the diamond from an output surface including at least one of the table or the crown.

FIG. 5B shows example optical paths of light rays from the virtual camera 406 of FIG. 4 through the diamond of FIG. 3A. Since optics is reversible, a ray traced from the virtual camera 406 to the selected facet 352 can be no different from a ray leaving the facet 352 and going to the virtual camera. In some cases, it is easier to implement by tracing rays starting at the virtual camera 406. As diagrams B1-B5 show, the paths to the virtual camera 406 and the paths from the virtual light source 404 turn out to be very similar.

Figures 6A, 6B:
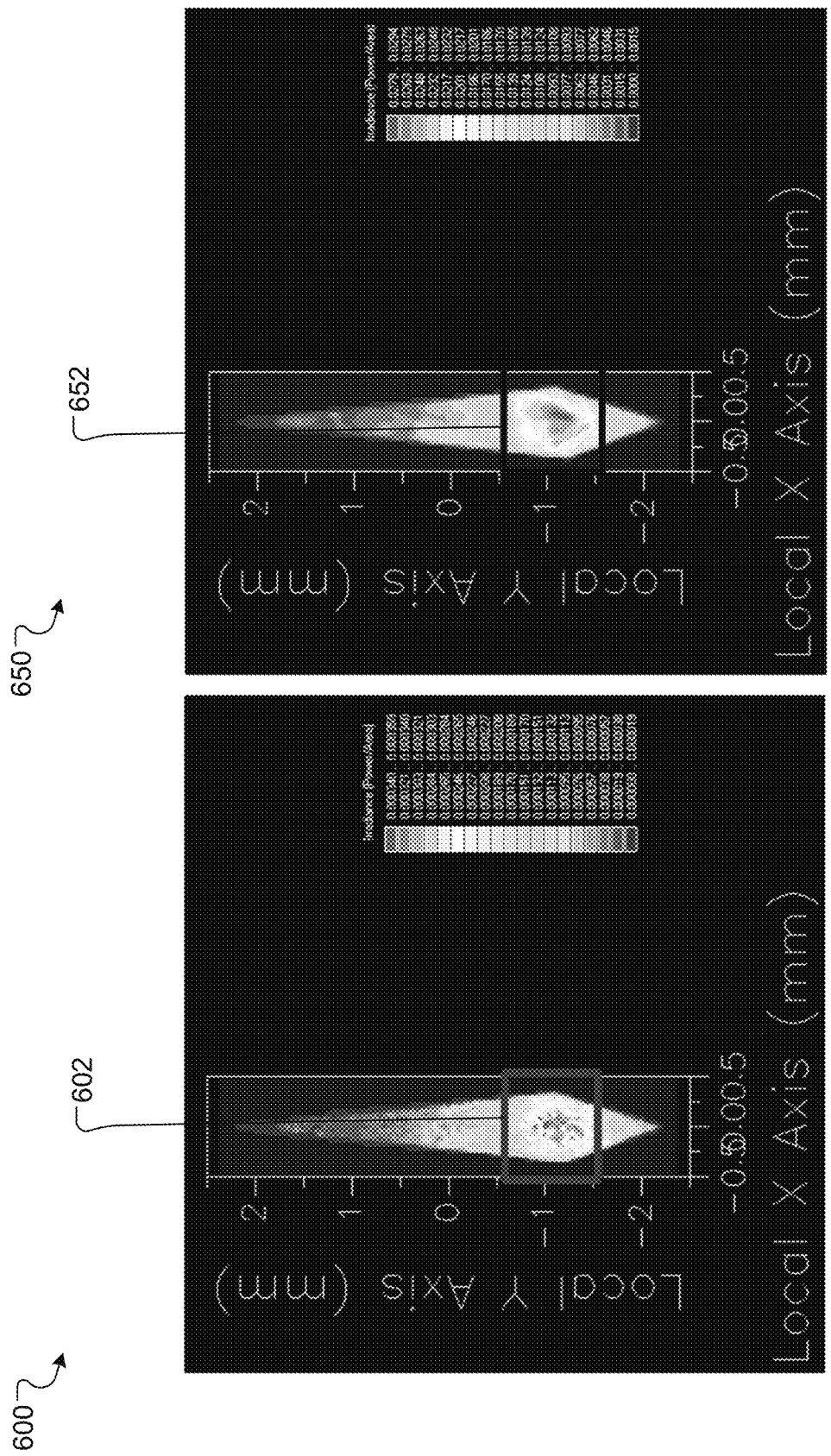
FIG. 6A shows an irradiance plot detected on the virtual camera representing light reflection distribution on the selected facet for light from the virtual light source.
FIG. 6B shows an irradiance plot detected at the virtual light source representing light reflection distribution on the selected facet for light from the virtual camera.

FIGS. 6A-6B show example irradiance (power per area) plots 600 and 650 representing light reflection distributions on the selected facet 352 for light from the virtual light source (6A) and from the virtual camera (6B), respectively. It is shown that a region 602 encloses most of the energy. That is to say, on the selected facet 352, the light is reflected most by the region 602. Thus, if a diffractive structure is arranged on the region 602, the diffractive structure can have a most significant effect on the optical performance of the diamond. As noted above, an optical value can be defined as a ratio of energy enclosed in the region and a total energy enclosed in the facet. The region 602 is identified to have a higher optical value than one or more other regions on the facet 352 and thus can be determined to be arranged with a diffractive structure. As an example, the optical value of the region 602 is about 70%. A maximum irradiance of the selected facet 352 lies at a center of the region 602. The center is closer to the culet of the diamond than the girdle of the diamond. In a particular example, the center of the region 602 is about 1 mm away from the culet. Plot 650 is similar to plot 600 and has a region 652 located near the culet.

Figure 7B:
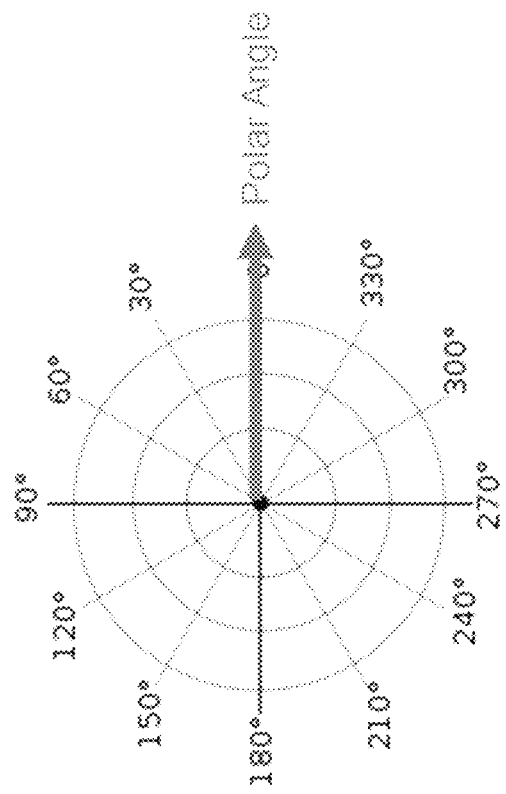
FIGS. 7A-7C show spatially variant angle information for the light reflection distribution of FIGS. 6A-6B.
Figure 7A:
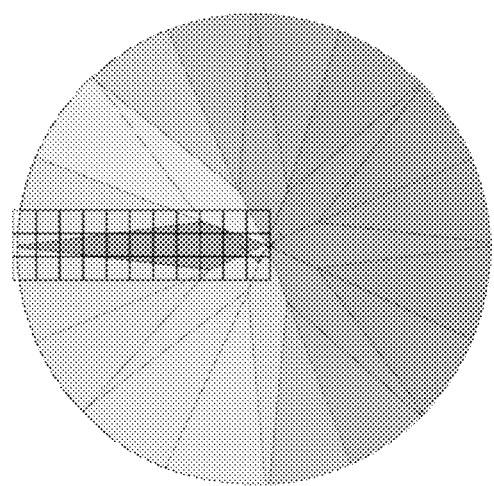
Figure 7C:
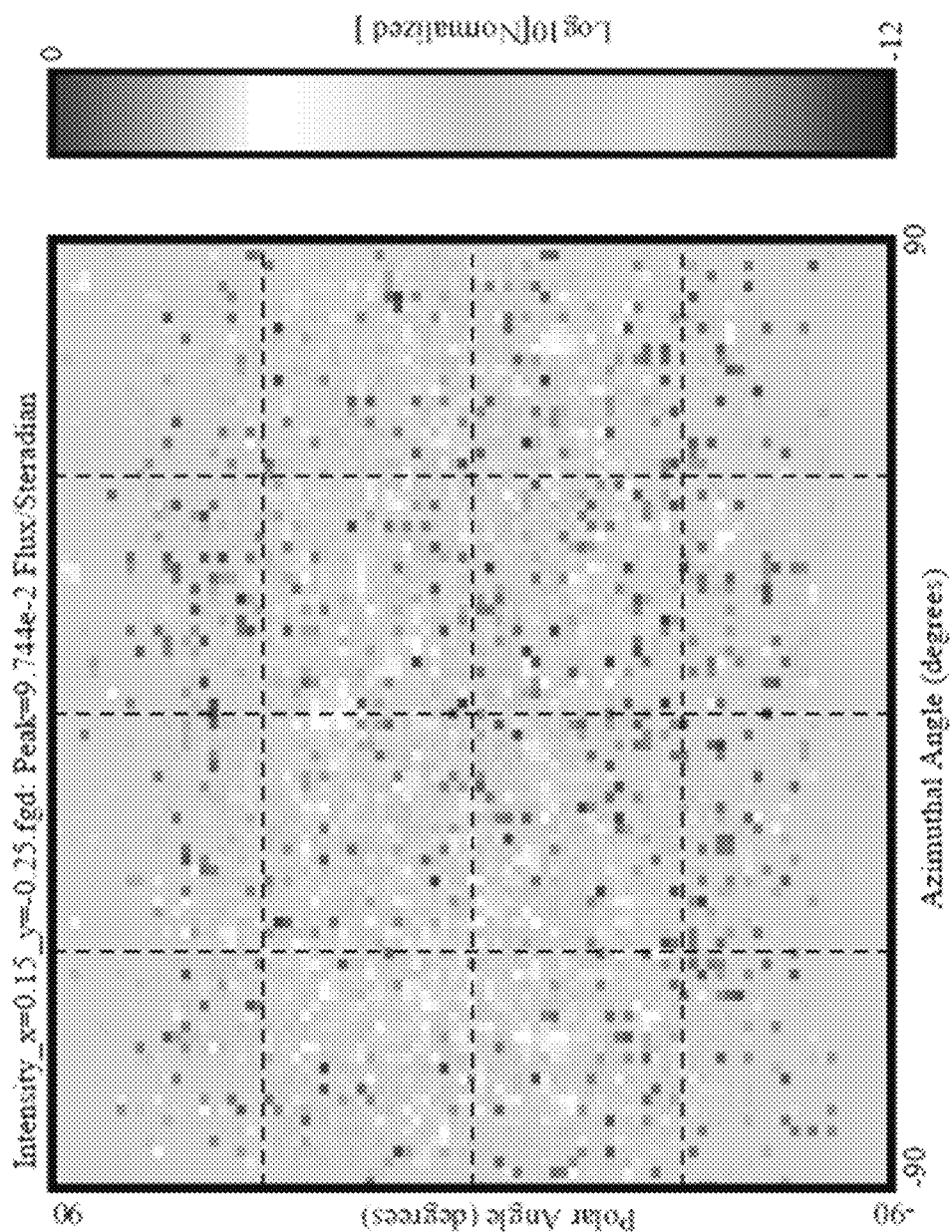
Figure 8:
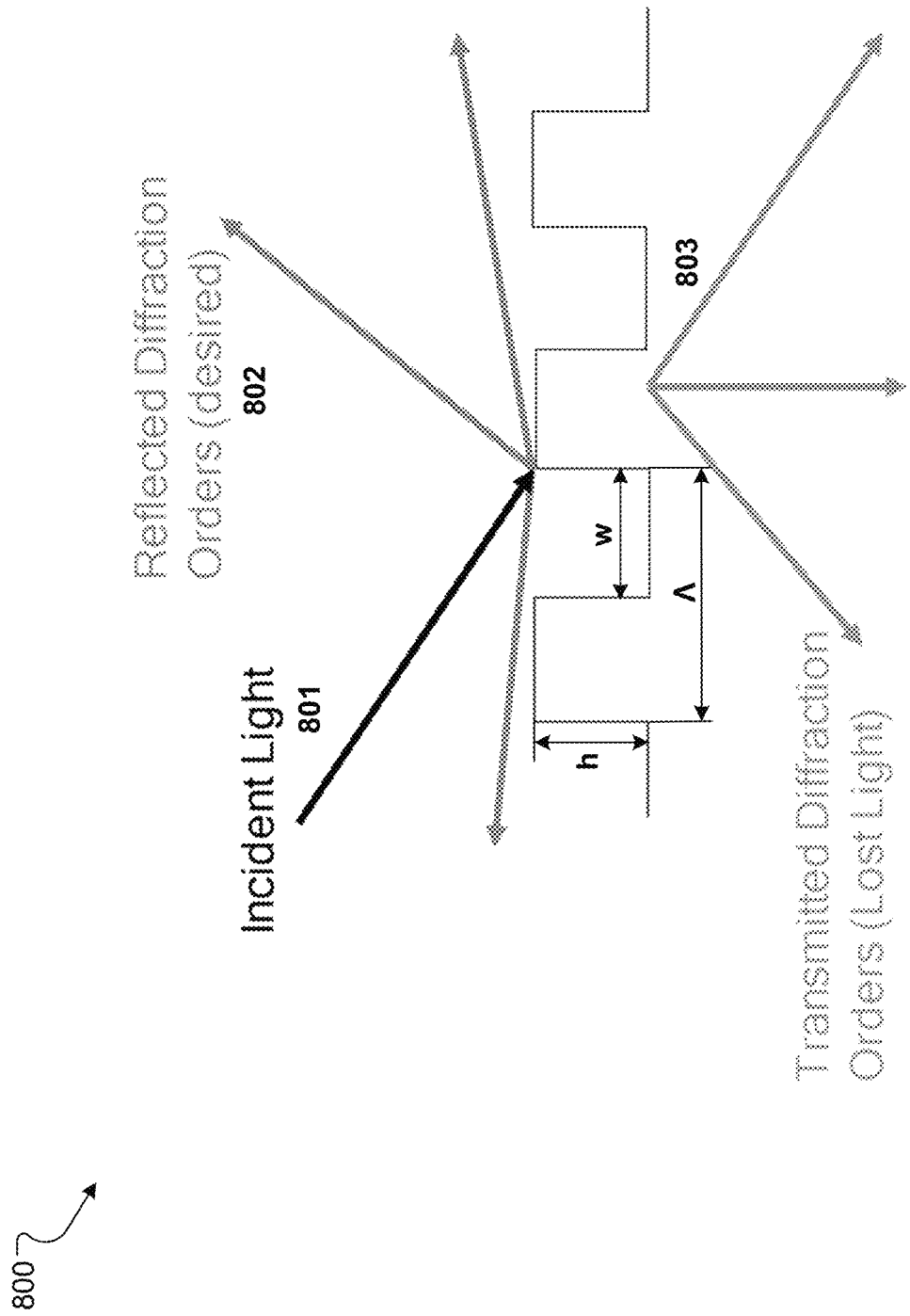
FIG. 8 is a schematic diagram of an example diffraction grating.

FIGS. 7A-7C show example spatially variant angle information for the light reflection distribution of FIGS. 6A-6B. Angles at which the light comes from and contributes to the light reflection distribution on the selected facet are analyzed. Instead of analyzing one large surface on the facet 352, the facet 352 is tiled with a larger number of small surfaces (as shown in FIG. 7A). A set of rays are traced, then an angle plot is generated for each of the sub-facets showing the angles of incidence for each part of the facet. The angle plots cover the whole hemisphere and are in elevation (polar) and azimuth coordination system (as shown in FIG. 7B). The light simulation algorithm can make the angle plot by mapping the azimuth angles to a first axis and similarly maps the elevation (polar) angles to a second axis perpendicular to the first axis (as shown in FIG. 7C). The angle plots can be analyzed to determine where the light energy is located and what directions the rays come from or go to. The analysis result shows that rays from the virtual light source 404 and rays from the virtual camera 406 follow very similar paths. There can be a small number of angles which have noticeably more energy, where a diffractive structure can be configured to steer the light from these angles to the output surface by beam steering.

Example Diffractive Structure

FIG. 8 is a schematic diagram of a diffraction grating 800 as an example diffractive structure. When an input light 801 is incident on the diffraction grating 800, the light 801 is diffracted into reflected light 802 and refracted (or transmitted) light 803, e.g., reflected into different diffractive orders and refracted into different diffractive orders. As the input light 801 is internally incident on a facet of the diamond, the reflected light 802 can eventually exit out of the diamond and contributes to the optical appearance of the diamond, which is desired, while the refracted light 803 is transmitted out of the diamond, which gets lost and is undesired. Thus, the diffraction grating 800 can be a reflective diffraction grating configured to reduce or eliminate the transmitted light 803. In some cases, at each diffractive order, the reflected light 802 is dispersed by the diffraction grating 800 into a spectrum of colors like a rainbow, including red, orange, yellow, green, blue and violet. As noted above, the colored reflected light can further travel through the diamond and exit from the diamond, which causes fire. In some cases, the reflected light is dispersed by the diffraction grating 800 into a special dominant color, e.g., red, blue, violet, or any other suitable color, which makes the diamond appear the special color. The reflected light can be also be dispersed by the diffraction grating 800 into two or more special colors.

The diffraction grating 800 has a period Λ and a peak-to-peak depth h. A width of grating feature (e.g., recess) in the diffraction grating 800 is w. In some cases, as shown in FIG. 8, the diffraction grating 800 has a square profile, and w is equal to Λ/2. In some cases, a diffraction grating with a differently shaped profile can be used, which can be dependent upon a desired beam steering effect, diffractive effect, and/or dispersive effect. For example, the diffraction grating 800 can have a sinusoidal profile, a saw-tooth profile, or any other suitable profile. In some cases, a diffraction grating is a blazed grating with a blazed angle, which can be optimized to achieve maximum grating efficiency in a given diffraction order. The blazed grating can be used as the diffractive structure to be arranged on the selected facet 352 of the diamond for beam steering to maximize the amount of light out of the diamond.

In a particular example, the grating period Λ can be 1 μm or larger. The grating depth h can be no more than 100 nm, and the grating 800 can be created in about 1.1 mm square region on a selected facet.

Example Simulations for Determining Diffractive Structures

Simulation can be performed to determine a diffractive structure (e.g., a diffraction grating 800 of FIG. 8) for an identified region on a surface of the diamond. The simulation can be performed by a software implementing the light simulation algorithm described above. As discussed above, one or more parameters of the diffraction grating 800, including a period, a width, a depth, an orientation, and a blazed angle, can be adjusted by the simulation to enhance or maximize the optical performance of the diamond that can include at least one of brilliance, fire, color, or sparkle.

Figure 9B:
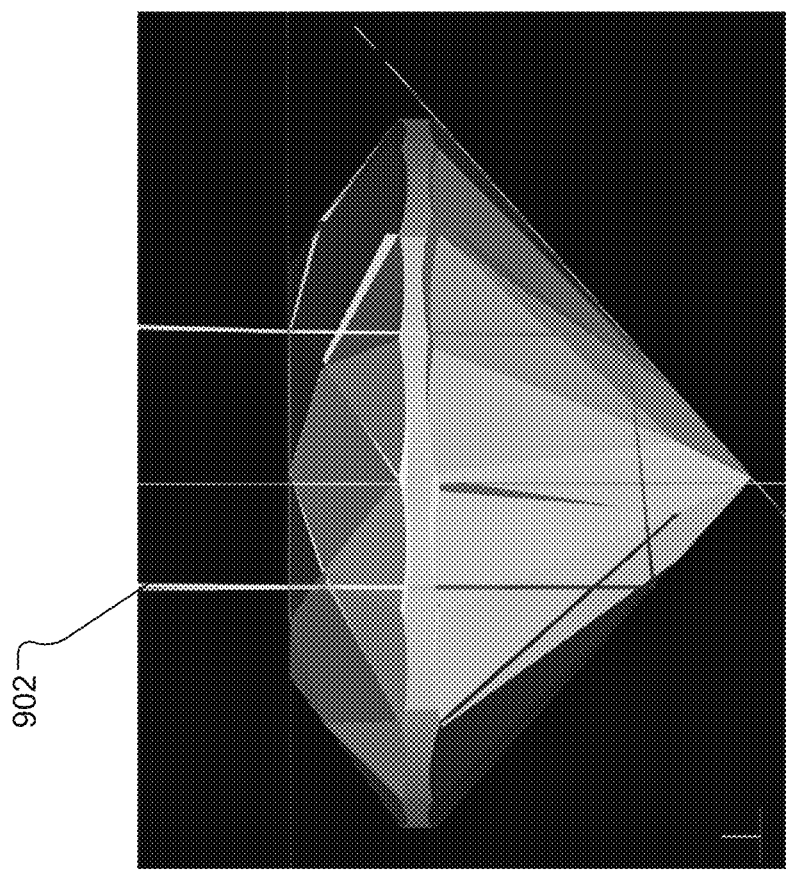
FIG. 9B shows an optical path with the grating of FIG. 9A on the selected facet.
Figure 9A:
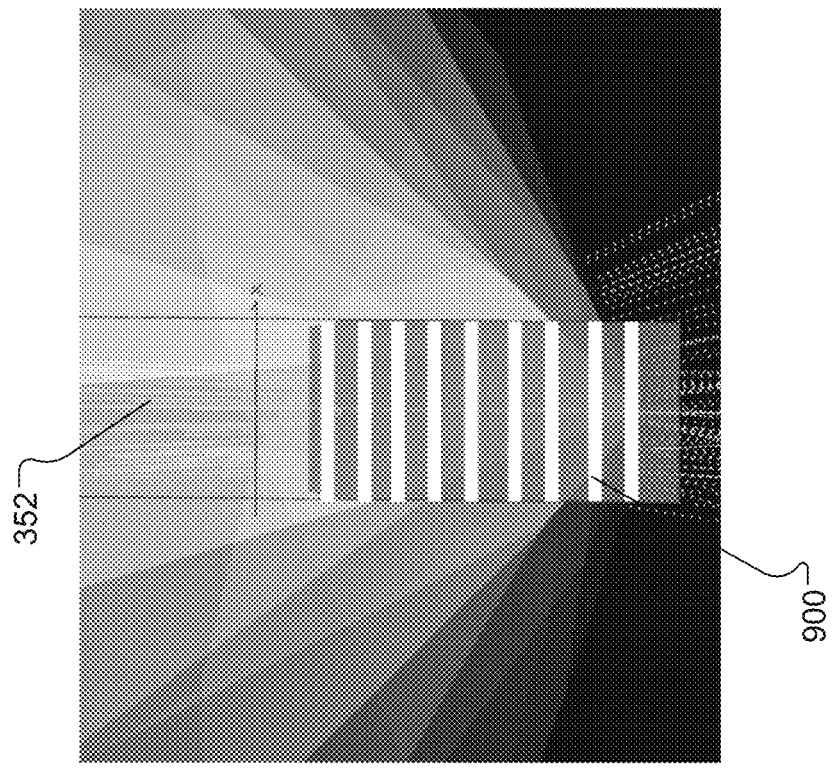
FIG. 9A shows an example diffraction grating with 0 degree orientation arranged on the selected facet of the diamond.

For example, the grating period can determine angles at which the diffracted orders appear. The grating period can be adjusted such that light at a particular diffracted order travels toward the virtual camera 406. In such a way, the grating can work close to the Littrow condition. The grating depth can affect a diffraction efficiency of the grating, and can be adjusted such that the grating depth can generate the largest diffraction efficiency. The orientation of the grating can also affect the optical performance of the diamond, as discussed below, FIG. 9A shows an example diffraction grating 900 with 0 degree orientation arranged on the selected facet 352 of the diamond. The grating 900 can be marked as 0 degree grating. The grating 900 can be similar to the grating 800 of FIG. 8. The grating 900 can have a depth of 100 nm, and a period of about 1.5 μm. The selected facet 352 extends from the culet to the girdle along an extending direction, and the 0 degree orientation of the grating 900 is perpendicular to the extending direction. The light at $-1^{st}$ diffracted order reflected by the grating 900 can be engineered to partially reach the virtual camera 406, as illustrated by optical path 902 of FIG. 9B. The diffraction efficiency for the reflected light at the $-1^{st}$ diffracted order can be up to 0.3.

Figure 10B:
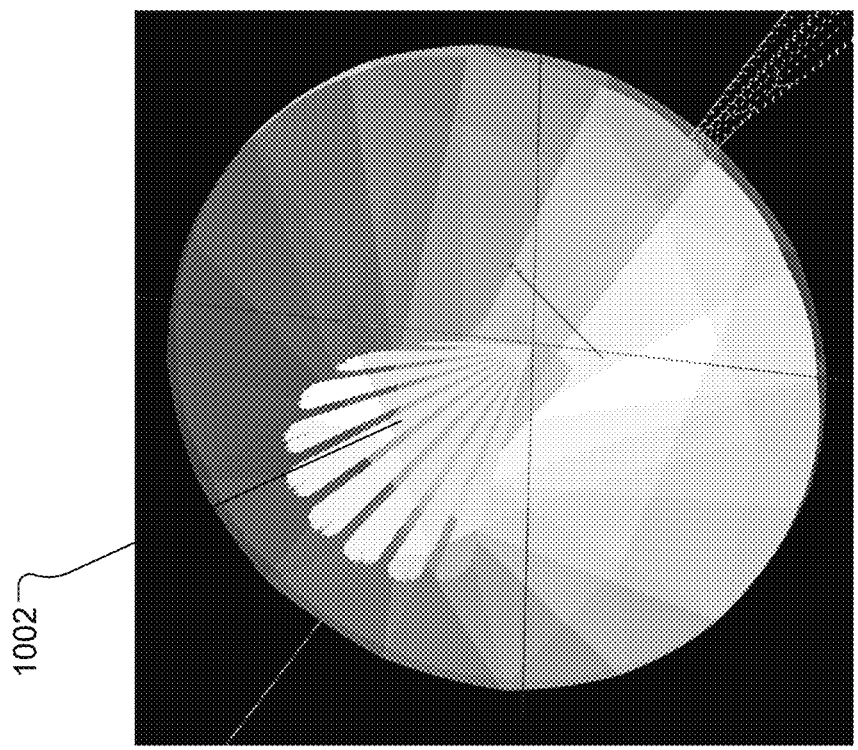
FIG. 10B shows a diffracted light pattern with the grating of FIG. 10A on the selected facet.
Figure 10A:
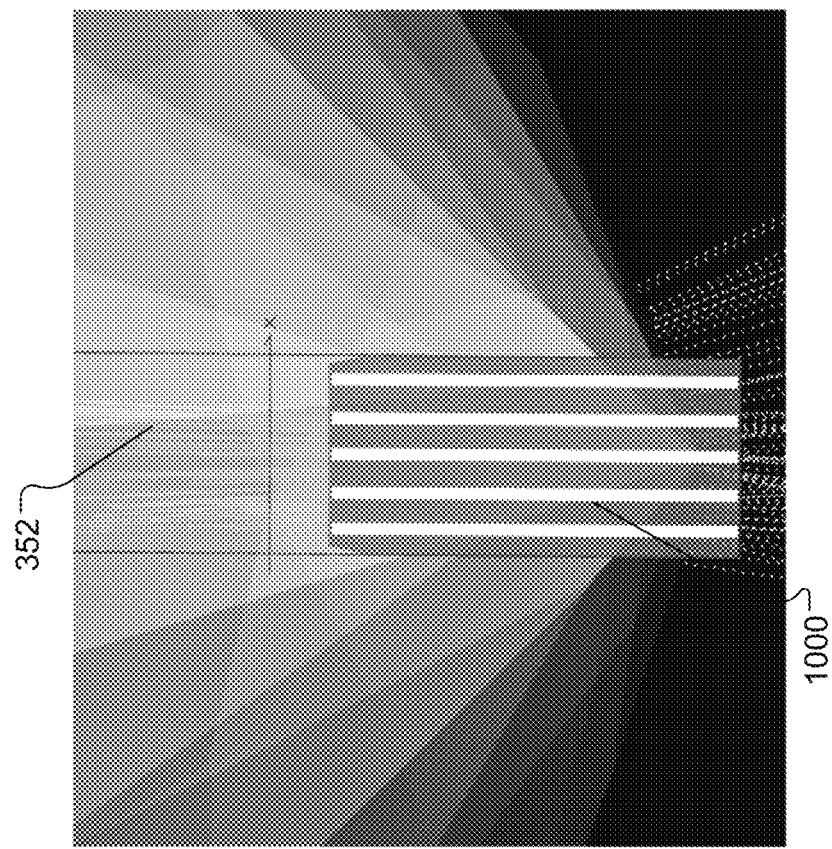
FIG. 10A shows an example diffraction grating with 90 degree orientation arranged on the selected facet of the diamond.

FIG. 10A shows another example diffraction grating 1000 with 90 degree orientation arranged on the selected facet of the diamond. The grating 1000 can be marked as 90 degree grating. The 90 degree orientation of the grating 1000 is parallel to the extending direction. The light incident on the grating 1000 with 90 degree orientation can be totally reflected to a fan of rays 1002, as illustrated in FIG. 10B. The grating 1000 may direct less amount of light back to the virtual camera 406 than the grating 900. In some implementations, a grating having an orientation at an angle is configured to totally reflect light internally in the diamond.

Figure 11B:
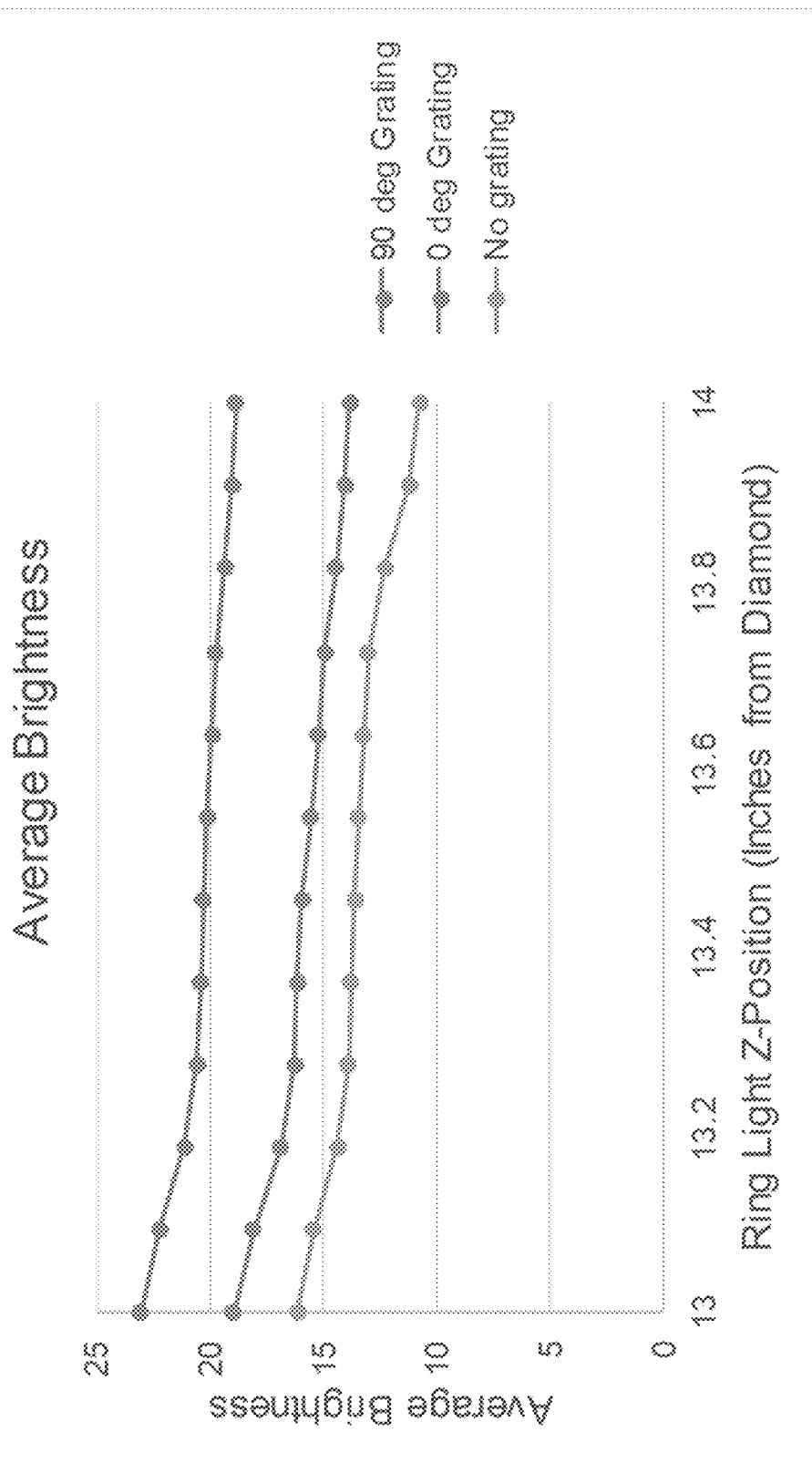
FIG. 11B shows plots of average brightness of the optical appearances of the diamond as a function of a position of the virtual light source.

FIG. 11A shows example data detected on the virtual camera representing optical appearances of the diamond arranged with 0 degree grating (a), no grating (b), and 90 degree grating (c) on the selected facet, respectively. From the optical appearances, average brightness of the diamond can be calculated. FIG. 11B shows plots of average brightness of the optical appearances of the diamond as a function of a position of the virtual light source. The plots show that the diamond with 0 degree grating can have a higher brightness than the diamond with 90 degree grating, which can have a higher brightness than the diamond without grating.

Figure 11C:
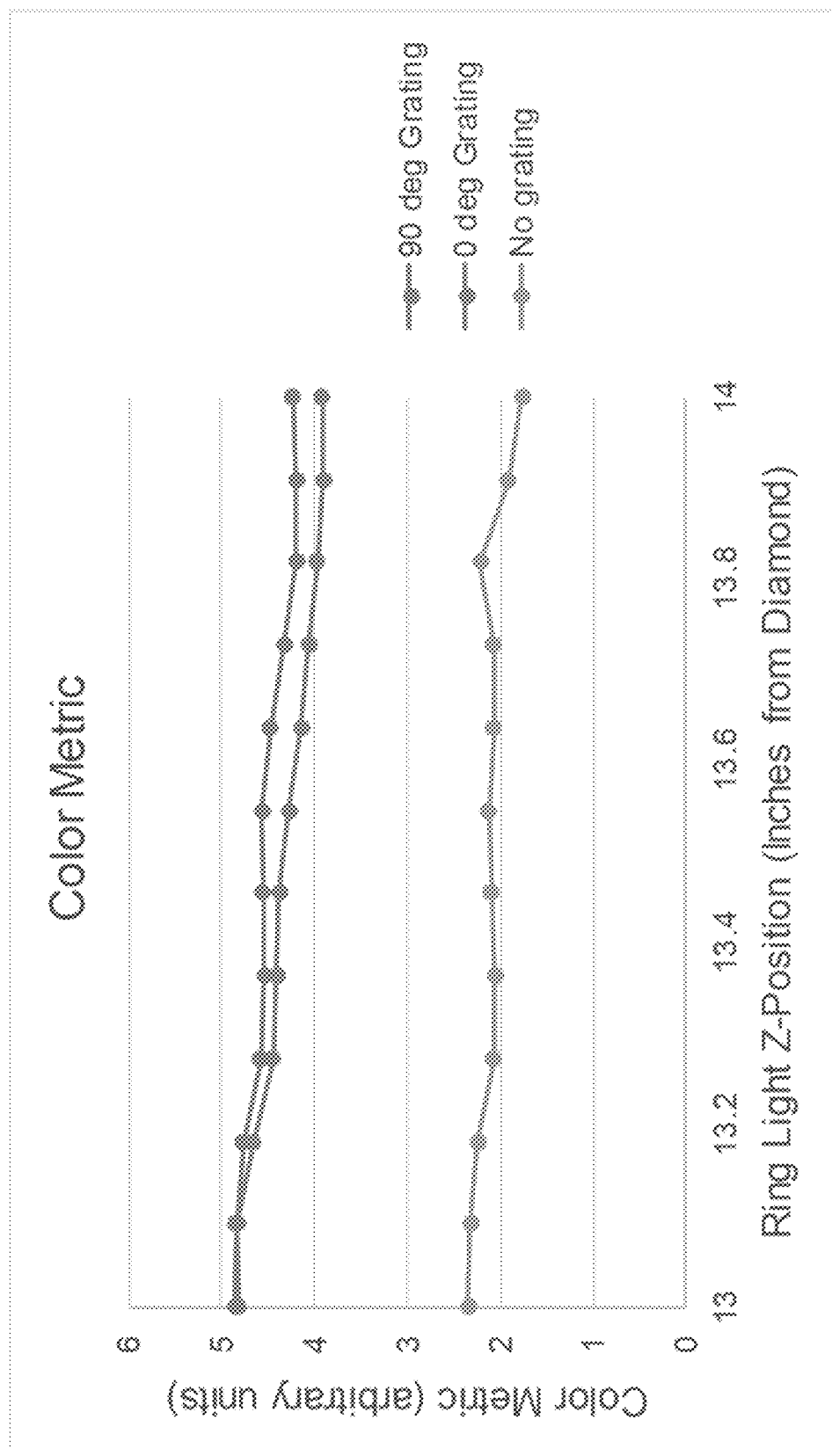
FIG. 11C shows plots of average color of the optical appearances of the diamond as a function of a position of the virtual light source.

From an optical appearance, e.g., diagram (a) of FIG. 11A, a color metric can be created as follows to measure how colorful the diamond is. If a pixel is a shade of gray, then the R (red), G (green), B (blue) values are identical. R, G, B values can be obtained from R, G, B channels of the optical appearance. Mean of the R, G, B values can establish the nearest gray value. Then a parameter is computed by taking the L2 Norm of the R, G, B vector with the mean subtracted. The mean of the parameters computed for all pixels in the optical appearance can be determined to be the color metric, which is marked as average color. FIG. 11C shows plots of average color of the optical appearances of the diamond as a function of a positon of the virtual light source. The plots show that the diamond with 0 degree grating can have a slightly more color than the diamond with 90 degree grating, which can have a significantly more color than the diamond without grating. That is, the diamond with the 0 degree grating or the 90 degree grating can cause more fire than the diamond without grating.

Figure 12A:
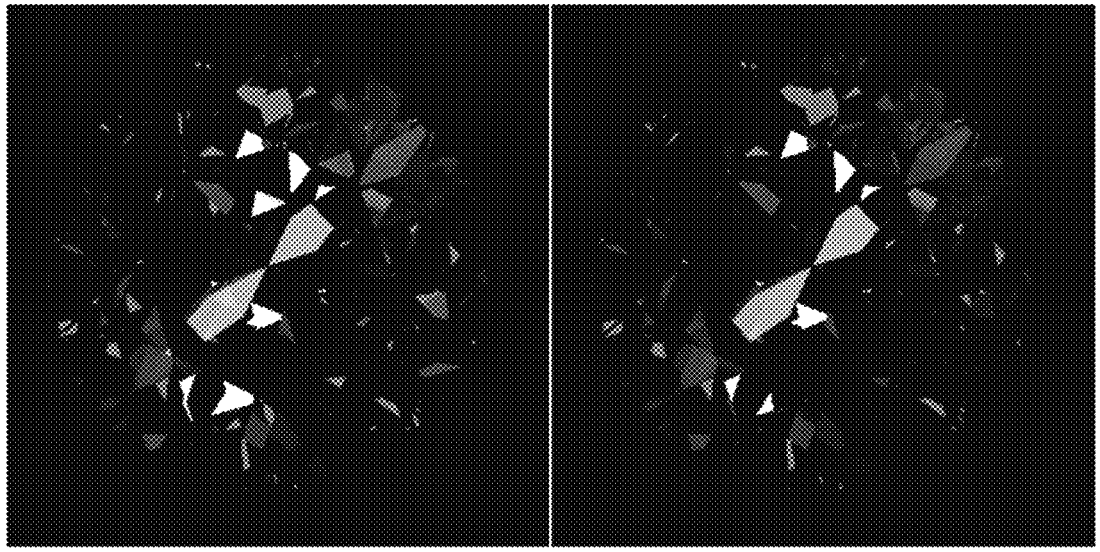
FIGS. 12A-12C show example changes of average brightness of the diamond arranged with 0 degree grating (12A), no grating (12B), and 90 degree grating (12C) on the selected facet.
Figure 12B:
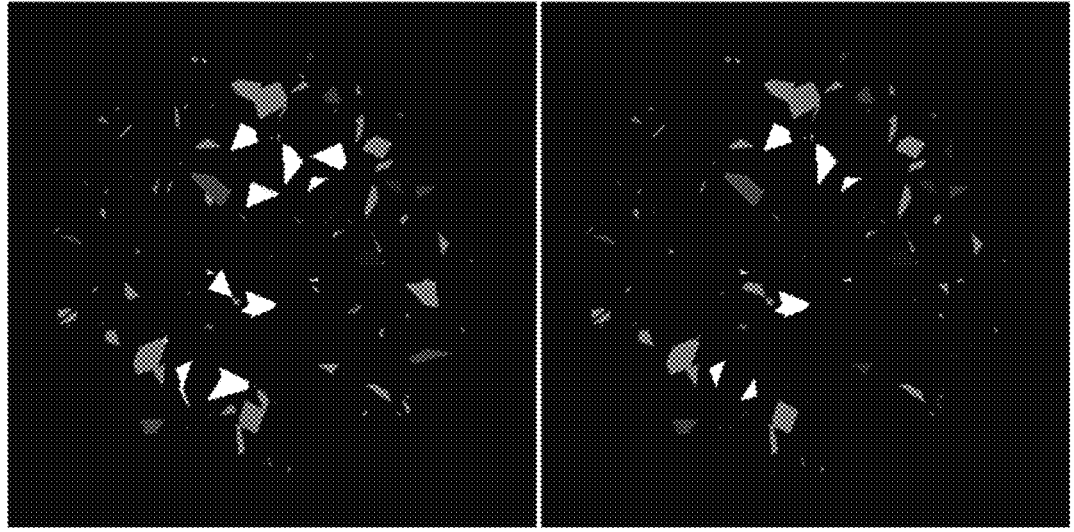
Figure 12C:
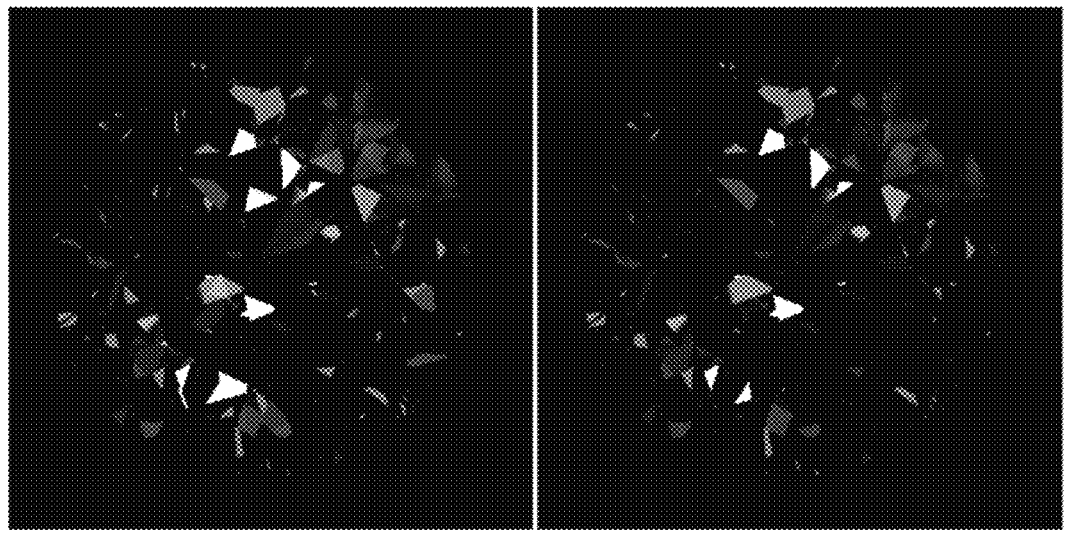

As noted above, the sparkle of the diamond can be determined by moving the virtual light source or the virtual camera and then determining a difference of the generated data before and after the moving. In this simulation, the virtual light source is moved, e.g., continuously, upward by 1 inch, and then the average brightness (and/or average color) of the optical appearance of the diamond at two ends of the range of movement, e.g., the first frame of the optical appearance and the last frame of the optical appearance, can be determined. Then the change of the average brightness (and/or average color) can be determined by comparing the average brightness of the first fame and the last frame. FIGS. 12A-12C show example changes of average brightness of the diamond arranged with 0 degree grating (12A), no grating (12B), and 90 degree grating (12C) on the selected facet, respectively. It is shown that the diamond without grating has more color percent change than the diamond with 90 degree grating, and the diamond with 90 degree grating has more color percent change than the diamond with 0 degree grating.

Figure 13B:
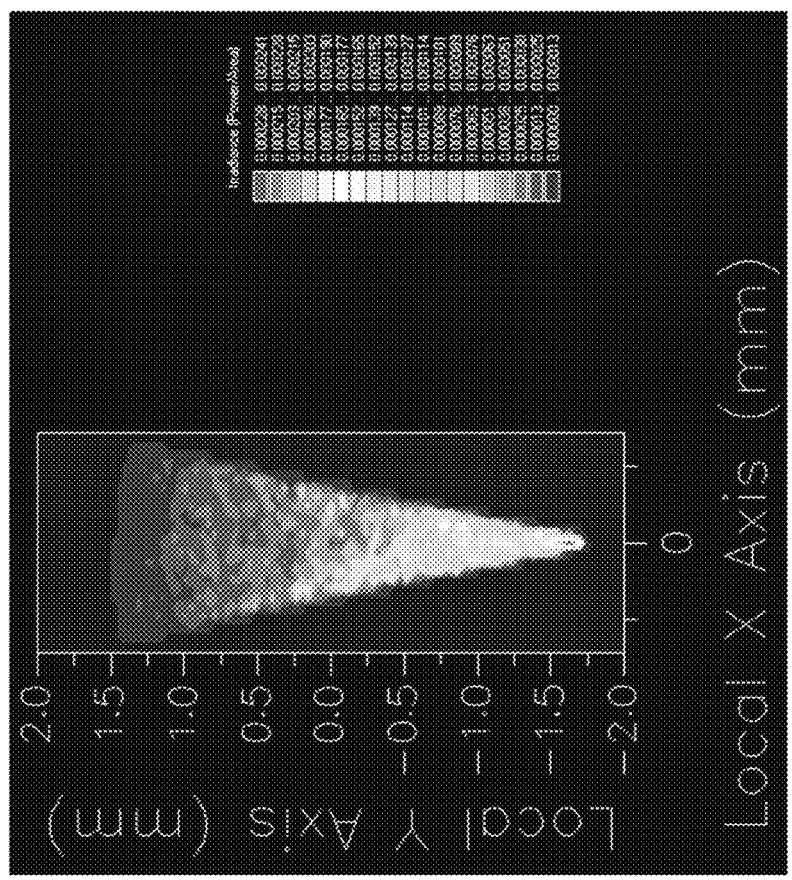
FIG. 13B shows an irradiance plot detected on the virtual camera representing light reflection distribution on the lower girdle facet for light from the virtual light source.
Figure 13A:
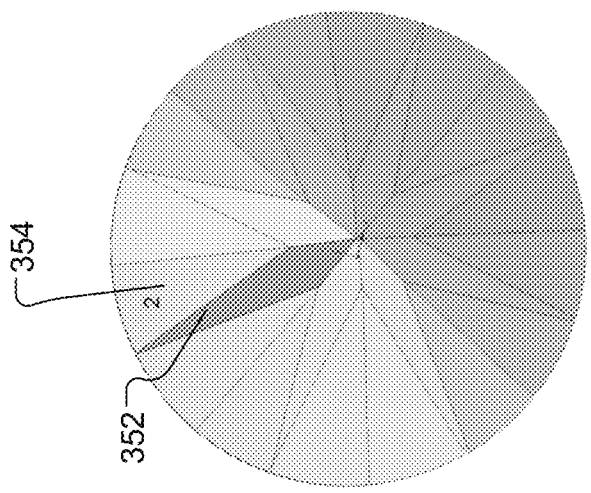
FIG. 13A shows a lower girdle facet on the pavilion of FIG. 3B.
Figure 14:
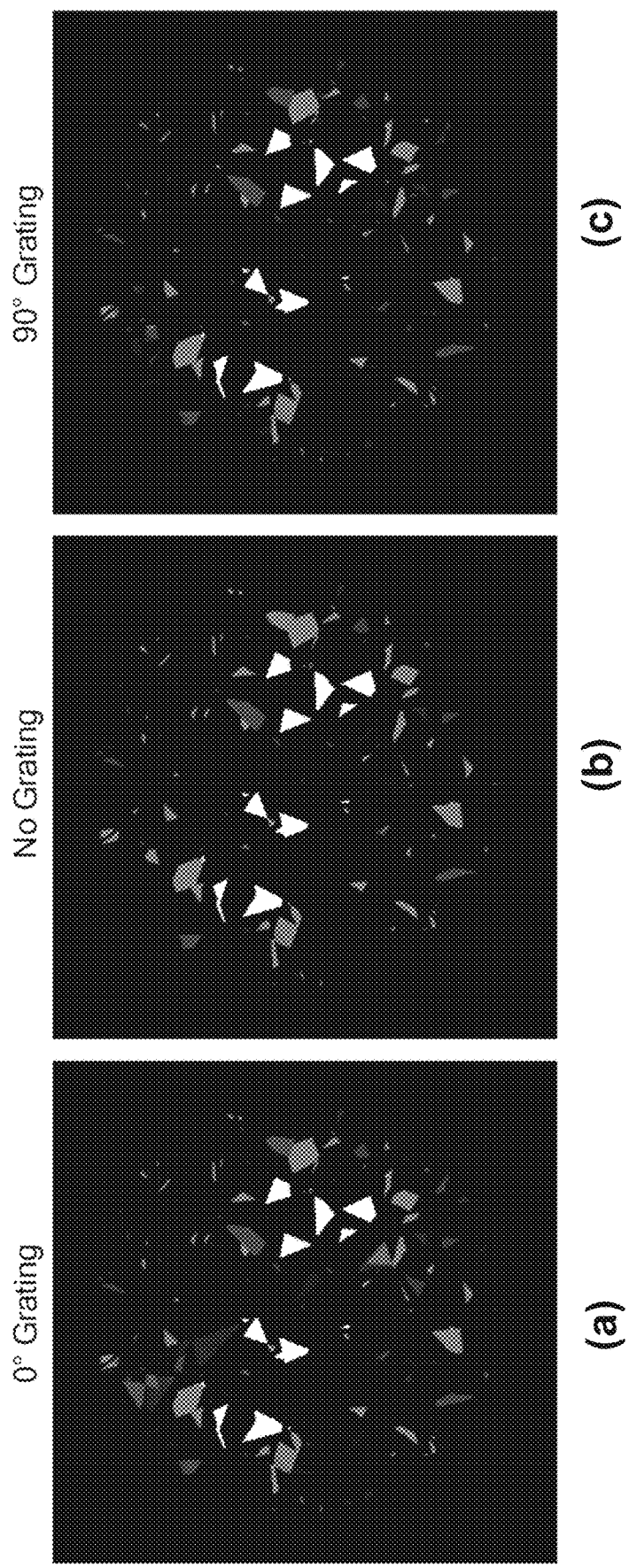
FIG. 14 shows example data detected on the virtual camera representing optical appearances of the diamond arranged with 0 degree grating (a), no grating (b), and 90 degree grating (c) on the lower girdle facet of FIG. 13A.

Besides the lower main facet 352, other surfaces on the diamond can be also considered to be arranged with a diffractive structure. FIG. 13A shows the lower girdle facet 354 on the pavilion of FIG. 3B. The lower girdle facet 354 is adjacent to the lower main facet 352. FIG. 13B shows an irradiance plot representing light reflection distribution on the lower girdle facet 354 for light from the virtual light source 404 to the virtual camera 406 of FIG. 4. However, compared to the irradiance plot representing light reflection distribution on the lower girdle facet 352, as shown in FIG. 6A, the total energy enclosed in the lower girdle facet 354 is dramatically lower than the total energy enclosed in the lower main facet 352. FIG. 14 shows example optical appearances of the diamond arranged with 0 degree grating (a), no grating (b), and 90 degree grating (c) on the lower girdle facet 354 of FIG. 13A. It is shown that, compared to the diamond without grating, the optical appearance (or the optical performance) of the diamond does not change much with 0 degree grating or 90 degree grating. Thus, the lower girdle facet 354 is less favorable than the lower main facet 352 to be arranged with a diffractive structure.

FIG. 15A shows a schematic diagram of eight lower main facets on the pavilion of FIG. 3B. The eight lower main facets are numbered as 1 to 8. The eight facets form four pairs of facets, including 1 and 5, 2 and 6, 3 and 7, and 4 and 8. On a planar view of the pavilion, the two facets in one pair are opposite to each other. Since the diffracted light from a facet can travel to the opposite facet and reflected by the opposite facet, as discussed above, one facet from a pair of facets can be selected to be arranged with a diffractive structure, and the other facet from the same pair can be left blank without arranging a diffractive structure, which can double the effect of the diffractive structure and minimize the light loss. In such a way, less number of diffractive structures can be determined and fabricated on the diamond, which can reduce cost and/or improve the optical performance of the diamond.

Figure 15C:
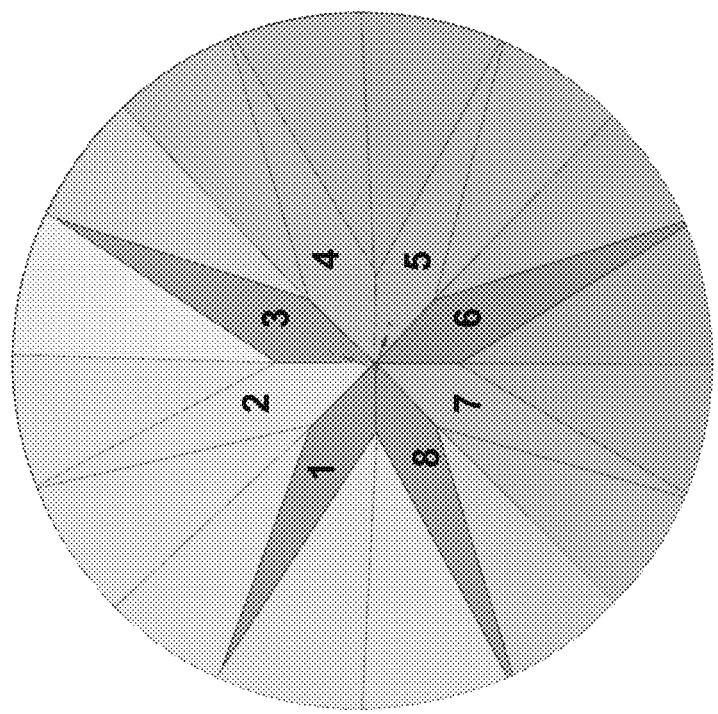
FIG. 15C shows another example of four lower main facets to be selected for diffractive structures.
Figure 15B:
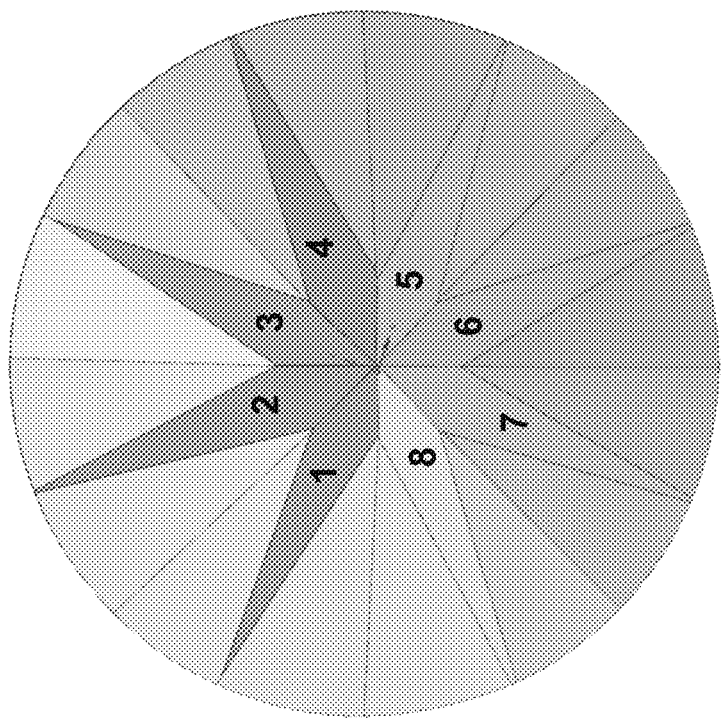
FIG. 15B shows an example of four lower main facets to be selected for diffractive structures.

In some cases, all the eight facets can be selected to be arranged with diffractive structures, as FIG. 15A shows. In some cases, one facet from each pair is selected to be arranged with a diffractive structure. For the eight lower main facets, four facets from the four pairs can be selected, as illustrated in FIGS. 15B and 15C. There can be different combinations of the four selected facets, for examples, facets 1, 2, 3, and 4 (as shown in FIG. 15B), facets 1, 2, 3, 8, facets 1, 2, 4, 7, facets 1, 3, 4, 6, and facets 1, 3, 6, 8 (as shown in FIG. 15C). Since the diffracted light from a facet can travel to the opposite facet and possibly to an adjacent facet, to maximize the optical performance of the diamond, the four selected facets can be evenly contributed around the diamond or the light reflection in the diamond can be balanced or uniformly distributed. As an example, for the eight facets 1 to 8, the selected four facets can be facets 1, 3, 6, and 8.

FIG. 16 show regions (1602 to 1608) with high optical values on the four selected facets of FIG. 15C, that is facets 1, 3, 6 and 8. For each facet, an irradiance plot representing light reflection distribution on the facet is calculated and a region enclosing 50% of the total energy is determined. That is, the high optical value is a ratio of 50%. For each facet, a curve is created around a perimeter of the determined region. This curve divides the facet into a grating region and a non-grating region.

Figure 17:
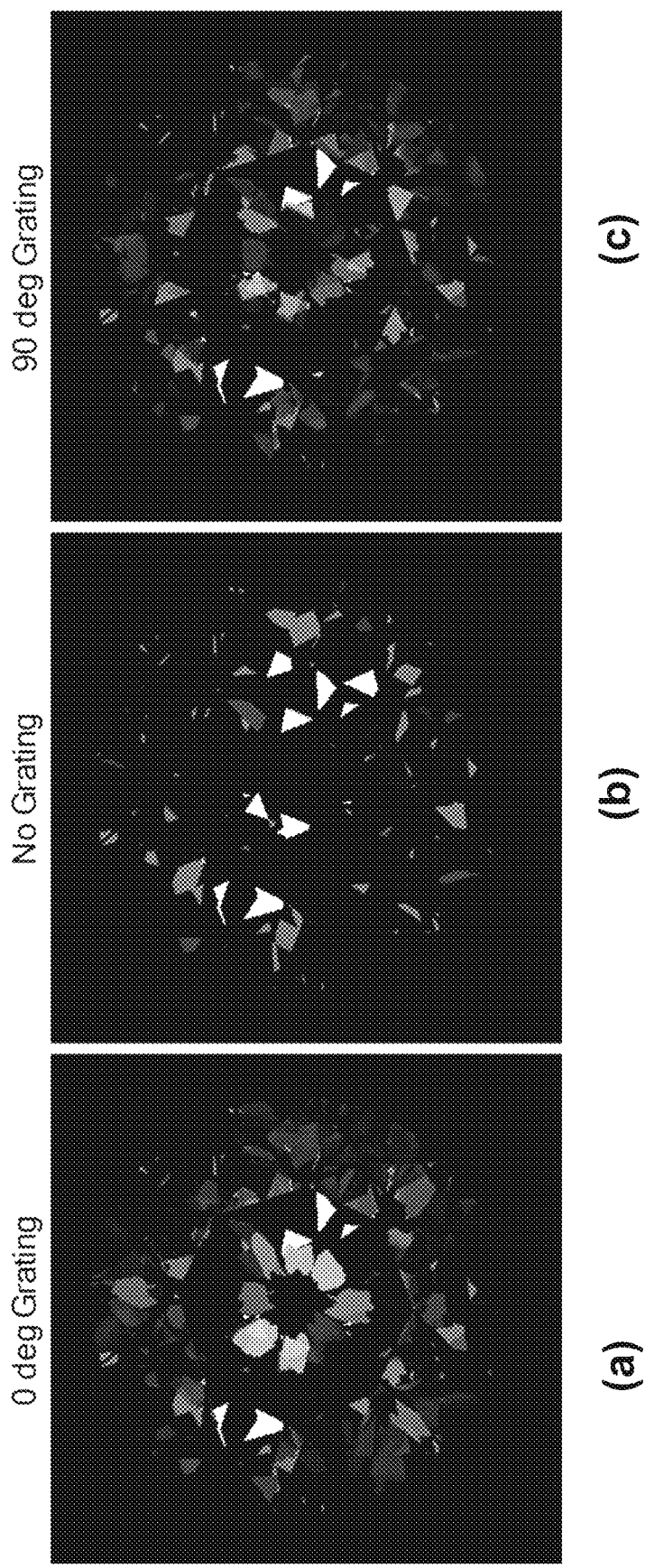
FIG. 17 shows example data detected on the virtual camera representing optical appearances of the diamond arranged with 0 degree grating (a), no grating (b), and 90 degree grating (c) on the regions of the four selected facets of FIG. 16.

FIG. 17 shows example optical appearances of the diamond arranged with 0 degree grating (a), no grating (b), and 90 degree grating (c) on the regions of the four selected facets of FIG. 16. It is shown that the diamond with 0 degree grating or 90 degree grating has more brightness and fire than the diamond with no grating.

Figure 18A:
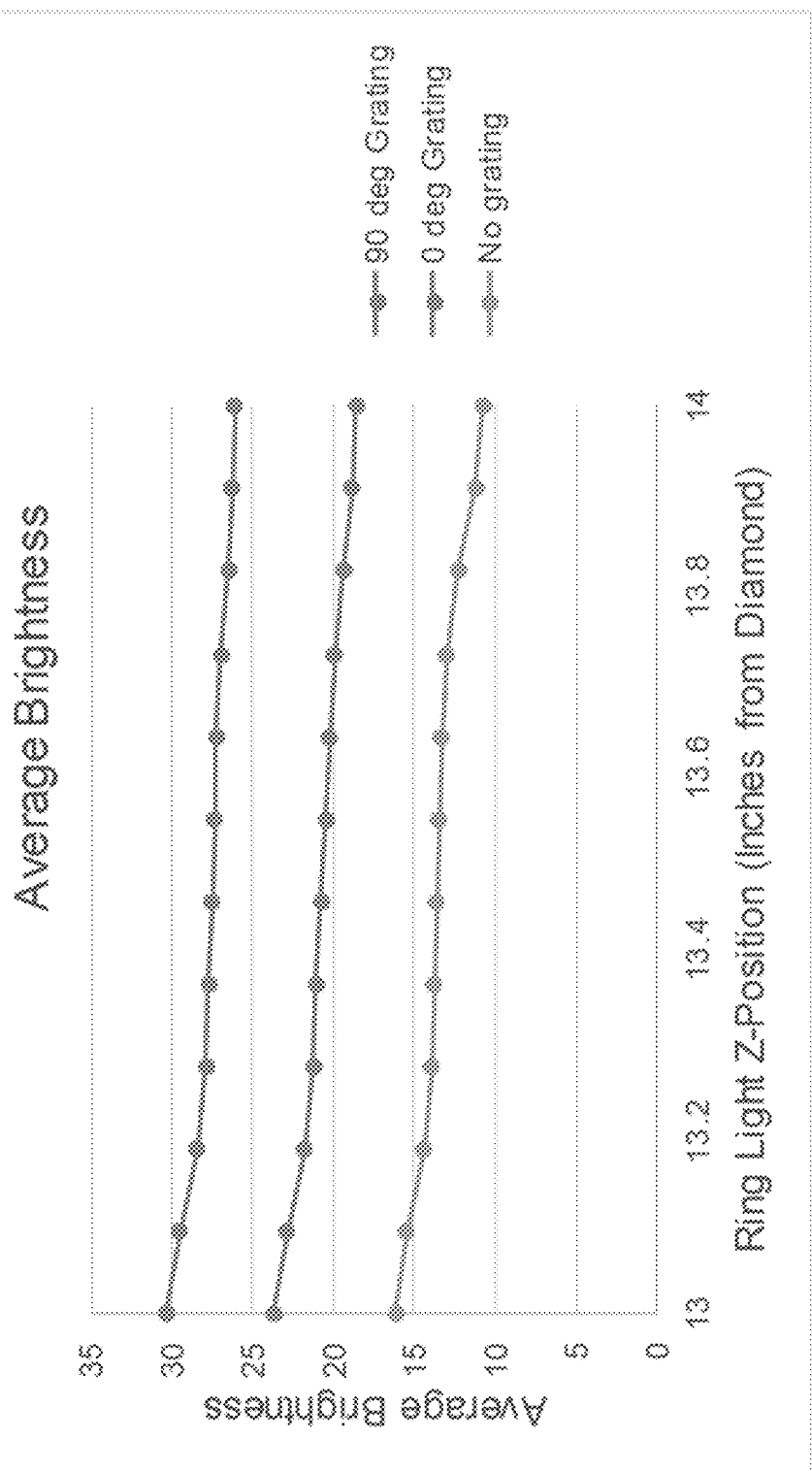
FIG. 18A shows example plots of average brightness of the optical appearances of the diamond as a function of a position of the virtual light source.

FIG. 18A shows plots of average brightness of the optical appearances of FIG. 17 as a function of the position of the virtual light source. It is shown that the diamond with 0 degree grating has more brightness than the diamond with 90 degree grating does, which has more brightness than the diamond with no grating. Moreover, compared to putting one grating on one facet, as shown in FIG. 11B, putting four gratings on four different facets causes more brightness.

Figure 18B:
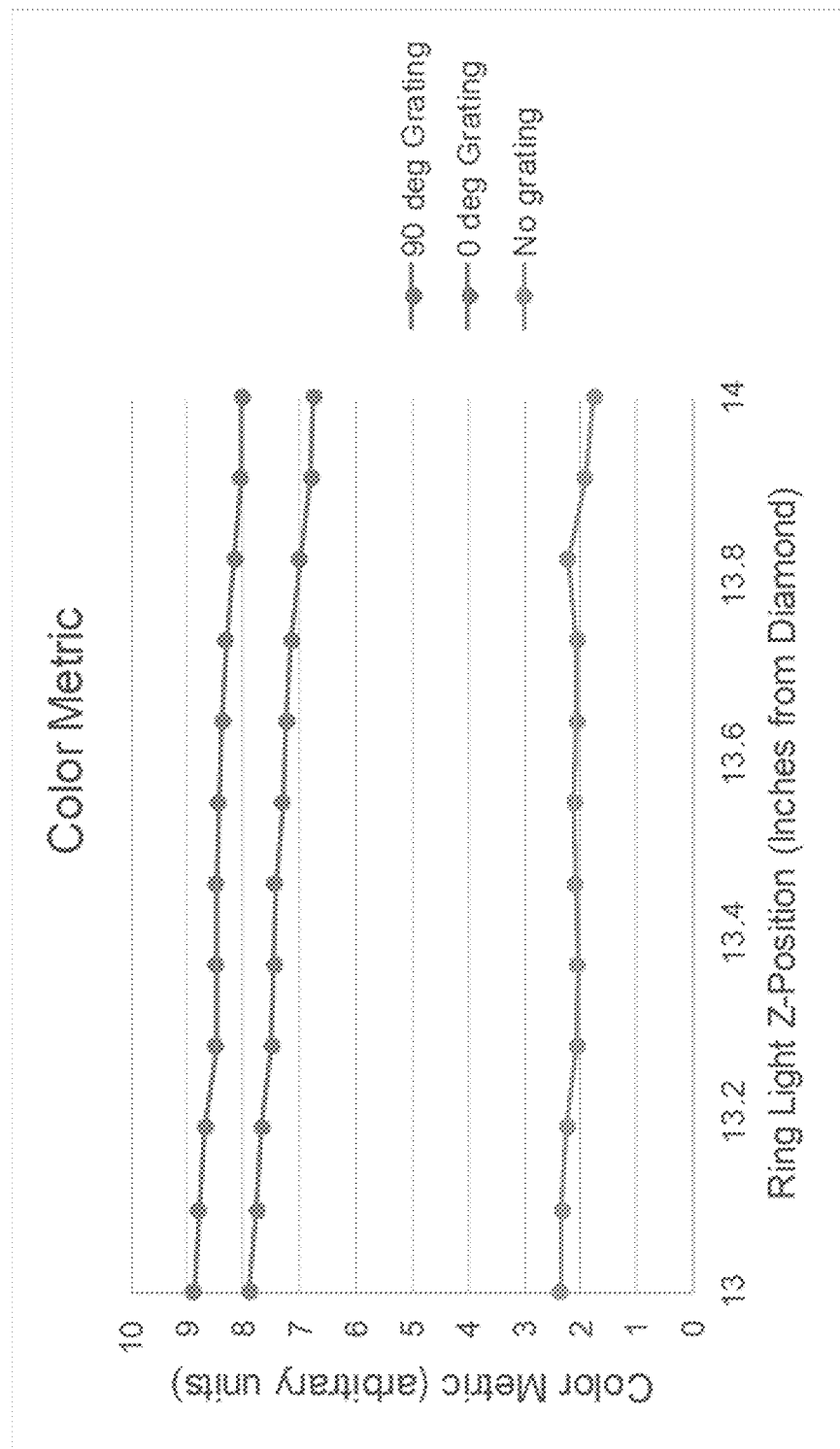
FIG. 18B shows example plots of average color of the optical appearances of the diamond as a function of a position of the virtual light source.

FIG. 18B shows plots of average color of the optical appearances of FIG. 17 as a function of the position of the virtual light source. It is shown that the diamond with 0 degree grating has more color (thus fire) than the diamond with 90 degree grating and the diamond with 90 degree grating has significantly more color (thus fire) than the diamond with no grating. Moreover, compared to putting one grating on one facet, as shown in FIG. 11C, putting four gratings on four different facets causes more color (thus fire).

Example Process for Fabricating Diffractive Structures on Gemstones

Figure 19A:
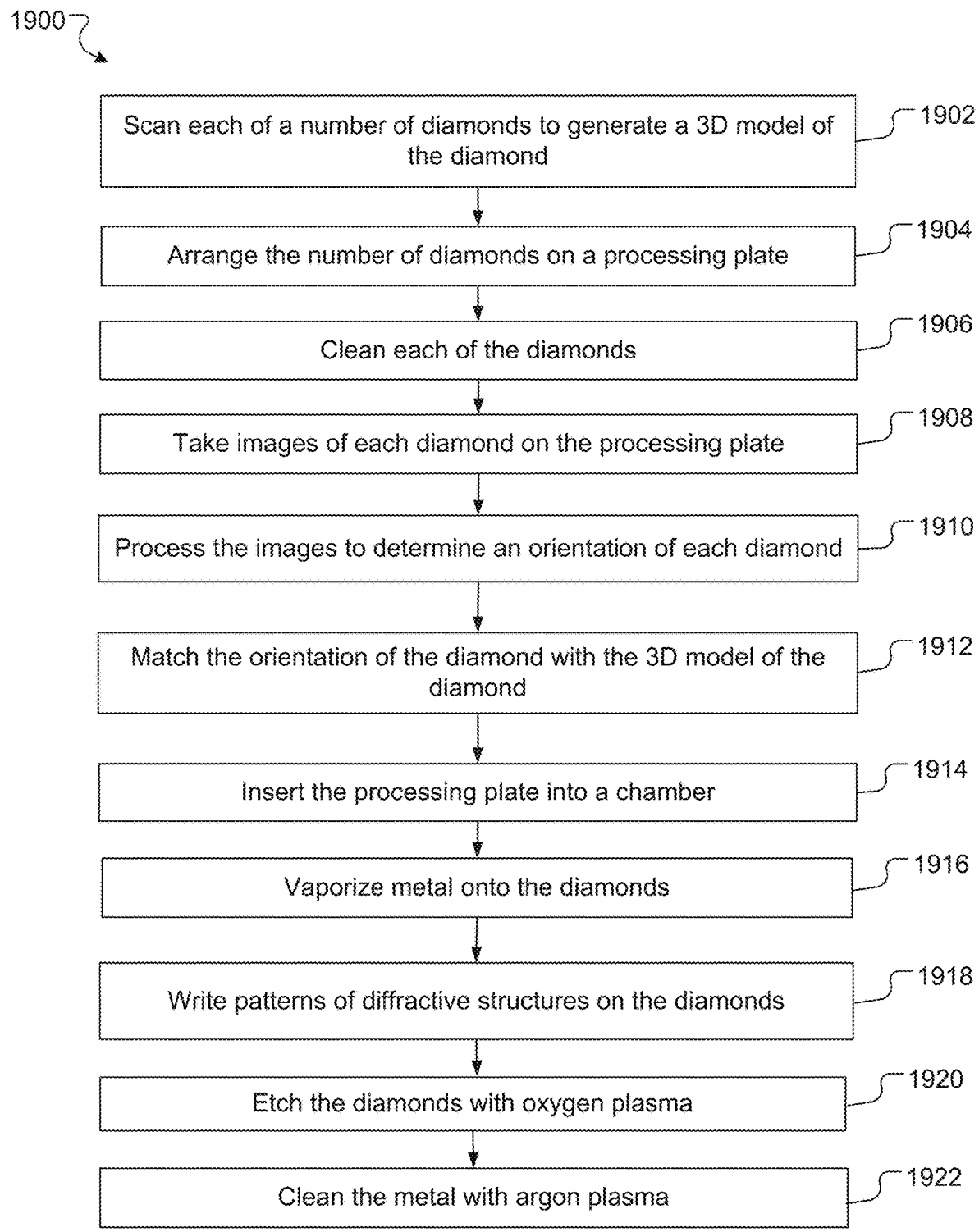

FIGS. 19A-19B are flowcharts of an example process 1900 of fabricating diffractive structures on a number of diamonds. FIGS. 20A-20G are schematic diagrams showing the example process of FIGS. 19A-19B. The process 1900 can be performed by a computing system and one or more fabrication machines, e.g., an FIB machine or a carbon milling machine. The process 1900 can improve manufacturing speed and lower manufacture cost.

Each of the number of diamonds is scanned to generate a 3D model of the diamond (1902). The generated 3D model of the diamond can be stored as a digital file, e.g., *STL file, in the computing system.

Figure 20A:
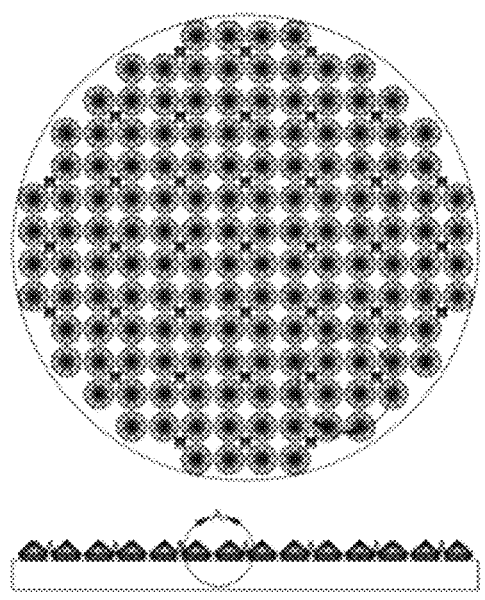

The number of diamonds are arranged on a processing plate (1904). The diamonds can be loaded and secured onto the processing plate, e.g., by adhesive material. In some cases, the processing plate has a number of recesses each sized to receive an individual diamond. The diamonds can be fit into the recesses without additional securing methods. FIG. 20A shows a top view and a side view of the diamonds arranged on the processing plate.

Each of the diamonds is cleaned (1906). For example, the diamonds on the processing plate can be carefully cleaned by soaking in a solvent (e.g., a piranha solution) and then boiling in sulfuric acid. The diamonds can be further cleaned by an RCA clean. In some cases, the diamonds can be also cleaned first before arranged on the processing plate.

Images of each diamond on the processing plate are taken (1908). Then the images are processed to determine an orientation of each diamond (1910). Based on the orientation of each diamond, a location of each facet of the diamond can be determined.

The orientation of the diamond is matched with the 3D model of the diamond (1912). In such a way, a region on a particular facet to be arranged with a diffractive structure in the 3D model can be matched with an area on a corresponding facet of the diamond. As discussed earlier, the region on the particular facet can be identified by analyzing the 3D model.

Figure 20B:
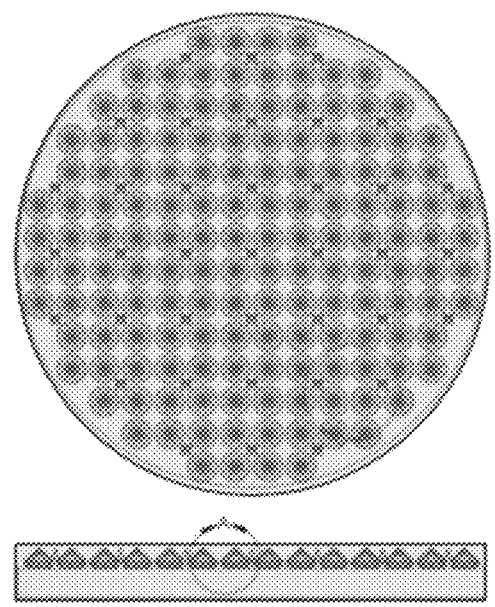

The processing plate with the diamonds is inserted into a chamber (1914). Then a metal, e.g., gold, is vaporized onto the diamonds (1916). The metal is used as a resist layer. FIG. 20B shows a view of the diamonds deposited with the vaporized metal layer.

Patterns of diffractive structures are written on the diamonds (1918). One or more diffractive structure can be fabricated on a diamond, and one or more diamonds can be processes to be arranged with diffractive structures. Note that step 1916 and step 1918 can occur in different chambers. FIG. 19B shows an example process to implement step 1918.

Referring to FIG. 19B, a diamond among the number of diamonds on the processing plate is selected to be processed (1952). Then a facet of the diamond is selected to be arranged with a diffractive structure (1954). As noted above, by analyzing the 3D model of the diamond, a region on the facet can be identified to be arranged with the diffractive structure. The facet is aligned (1956) such that a processing beam (e.g., an ion beam for an FIB machine) can be incident on the facet. The matching information between the orientation of the diamond and the 3D model of the diamond can be transmitted to the fabrication machine. The selected facet can be aligned by adjusting a moveable stage, e.g., an XYZ with rotation and azimuth stage, in the fabrication machine. FIG. 20C shows aligning the processing beam of the fabrication machine with the selected facet on the diamond. A bitmap divided into 9 areas can correspond to a shooting area of the processing beam. The processing beam can be moved to one of the bitmap areas and be focused onto a region on the bitmap area.

Figure 20E:
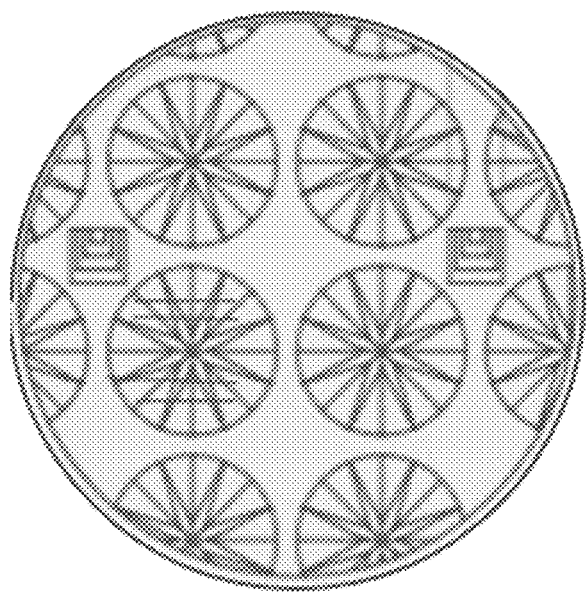

A region on the selected facet is identified (1958). The region on the facet to be arranged with a diffractive structure can be identified by the matching information between the orientation of the diamond and the 3D model of the diamond, such that the region on the facet is aligned with the processing beam of the fabrication machine. As FIG. 20D shows, bitmap area 1 is an autofocus feature and can be as a reference mark and bitmap area 2 is moved to the selected facet. Then the processing beam is focused onto the region on the selected facet to write a pattern of the diffractive structure on the region (1960). FIG. 20E shows a pattern of the fabricated diffractive structure on the region of the facet of the diamond.

After step 1960, the process 1900 returns to step 1954, which forms a first loop, to select another facet of the diamond for fabricating a diffractive structure. Then the first loop continues until all the facets previously selected for arranging a diffractive structure, e.g., the facets 1, 3, 6, 8 in FIG. 16, have been arranged with the corresponding diffractive structures, and then it is determined that processing the selected diamond is completed (1962). Then the process 1900 returns to step 1952, which forms a second loop, to select another diamond for processing. The second loop continues until all the diamonds previously selected for processing have been processed.

Figure 20F:
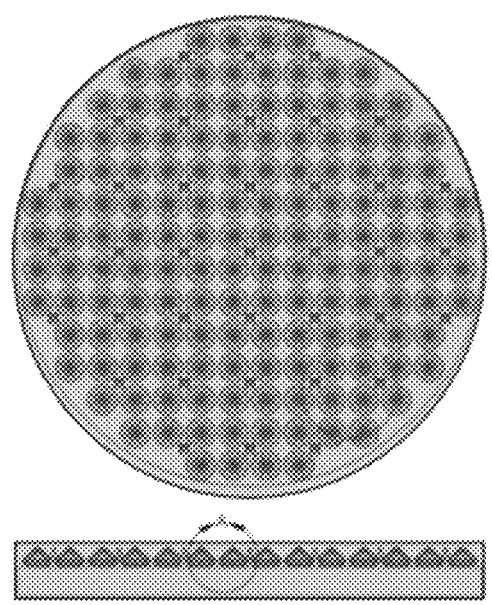
Figure 20G:
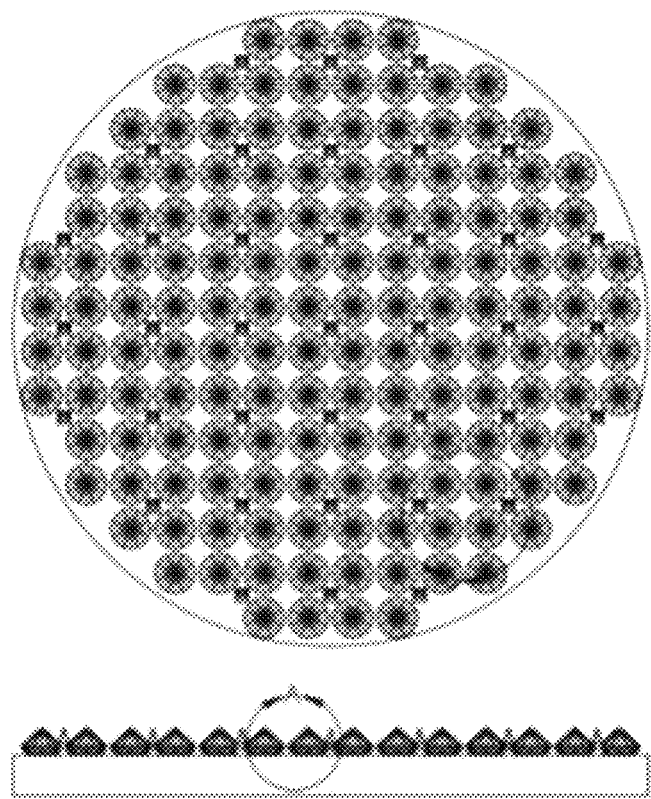

Referring back to FIG. 19A, after the patterns of diffractive structure are written on the diamonds, the diamonds are treated with oxygen plasma etching to etch the patterns into the diamonds (1920). FIG. 20F shows a view of the diamonds after the treatment of oxygen plasma etching. Finally the diamonds are cleaned by argon plasma (1922) to remove the metal resist layer. FIG. 20G shows the diamonds after the cleaning.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, such as, one or more modules of computer program instructions encoded on a tangible, non-transitory computer-storage medium for execution by, or to control the operation of, data processing apparatus. Alternatively or in addition, the program instructions can be encoded on an artificially generated propagated signal, such as, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, for example, a central processing unit (CPU), an FPGA (field programmable gate array), or an ASIC (application-specific integrated circuit). In some implementations, the data processing apparatus and special purpose logic circuitry may be hardware-based and software-based. The apparatus can optionally include code that creates an execution environment for computer programs, for example, code that constitutes processor firmware, a protocol stack, a database management system, an operating system, or a combination of one or more of them. The present specification contemplates the use of data processing apparatuses with or without conventional operating systems.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, such as, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD-R, DVD-RAM, and DVD-ROM disks. The memory may store various objects or data, including caches, classes, frameworks, applications, backup data, jobs, web pages, web page templates, database tables, repositories storing business and dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a cathode ray tube (CRT), liquid crystal display (LCD), light emitting diode (LED), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include multiple user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a web browser through which a user can interact with an implementation of the subject matter described in this specification, or any combination of one or more such back-end, middleware, or front-end components. The components of the system can be interconnected by any form or medium of wireline or wireless digital data communication, for example, a communication network. Examples of communication networks include a local area network (LAN), a radio access network (RAN), a metropolitan area network (MAN), a wide area network (WAN), worldwide interoperability for microwave access (WIMAX), a wireless local area network (WLAN) using, for example, 902.11 a/b/g/n and 902.20, all or a portion of the Internet, and any other communication system or systems at one or more locations. The network may communicate with, for example, internet protocol (IP) packets, frame relay frames, asynchronous transfer mode (ATM) cells, voice, video, data, or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and software, may interface with each other or the interface using an application programming interface (API) or a service layer. The API may include specifications for routines, data structures, and object classes. The API may be either computer language-independent or -dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in any suitable language providing data in any suitable format. The API and service layer may be an integral or a stand-alone component in relation to other components of the computing system. Moreover, any or all parts of the service layer may be implemented as child or sub-modules of another software module, enterprise application, or hardware module without departing from the scope of this specification.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing may be advantageous and performed as deemed appropriate.

Accordingly, the earlier provided description of example implementations does not define or constrain this specification. Other changes, substitutions, and alterations are also possible without departing from the spirit and scope of this specification.

What is claimed is:

1. A method of managing optical characteristics of a gemstone with diffractive structures, the method comprising:
    obtaining, by one or more processors, a three-dimensional model of the gemstone including representations of surfaces of the gemstone;
    identifying, by the one or more processors, a region on a surface of the gemstone having an optical value higher than one or more other regions on the surface of the gemstone by analyzing the three-dimensional model of the gemstone, wherein analyzing the three-dimensional model of the gemstone comprises:
        simulating propagation of an incident light through the gemstone and reflected by the surface;
        generating irradiance data representing light reflection distribution of the light on the surface;
        determining that a total energy enclosed in the surface of the gemstone is no smaller than a predetermined threshold; and
    determining, by the one or more processors, a diffractive structure to be arranged on the identified region of the surface of the gemstone, such that the gemstone with the diffractive structure has a higher optical performance than the gemstone without the diffractive structure.

2. The method of claim 1, wherein simulating the propagation of the incident light comprises:
    tracking, by using an algorithm, the light from a virtual light source to a virtual camera via one or more optical paths in the gemstone and internally reflected by the surface in the gemstone, wherein the irradiance data is detected on the virtual camera.

3. The method of claim 1, wherein identifying the region on the surface of the gemstone comprises: determining the region based on the generated irradiance data representing the light reflection distribution on the surface, wherein the optical value is defined as a ratio of an energy enclosed in the region and the total energy enclosed in the surface in the irradiance data, and
    wherein the method further comprises: determining that the optical value of the region on the surface of the gemstone is no smaller than a predetermined threshold that is determined based on one or more properties of the gemstone.

4. The method of claim 1, wherein a maximum irradiance of the surface is at a center of the region,
    wherein the gemstone is a diamond having a culet and a girdle, and the surface is a pavilion lower main facet, and the center of the region is closer to the culet of the diamond than to the girdle of the diamond.

5. The method of claim 1, wherein determining the diffractive structure to be arranged on the identified region of the surface of the gemstone comprises:
    simulating propagation of an incident light from a virtual light source to a virtual camera through the gemstone and diffracted by the diffractive structure on the identified region of the surface via one or more optical paths; and
    determining data detected on the virtual camera representing optical appearance of the gemstone.

6. The method of claim 1, wherein the diffractive structure comprises a diffraction grating configured to diffract the incident light into a reflected light with a plurality of angularly separated diffractive orders, and
    wherein the incident light comprises a white light, and the optical appearance comprises a distribution of light with different colors.

7. The method of claim 6, wherein the optical performance comprises at least one of brilliance, fire, color, or sparkle, and
    wherein determining the diffractive structure comprises determining one or more parameters of the diffractive structure such that at least one of:
        the optical appearance has a higher brilliance than the gemstone without the diffractive structure,
        the optical appearance has more fire than the gemstone without the diffractive structure,
        the optical appearance has a special color with a higher brightness than other colors compared to the gemstone without the diffractive structure, or
        the light distribution has more sparkle than the gemstone without the diffractive structure.

8. The method of claim 7, wherein determining the diffractive structure comprises at least one of:
    adjusting the one or more parameters of the diffractive structure to maximize the brilliance of the gemstone,
    adjusting the one or more parameters of the diffractive structure to maximize the fire of the gemstone,
    adjusting the one or more parameters of the diffractive structure to maximize the brightness of the special color of the gemstone, or
    adjusting the one or more parameters of the diffractive structure to maximize the sparkle of the gemstone.

9. The method of claim 7, wherein the one or more parameters comprise a period, a depth, a width, an orientation, a shape, and a blaze angle.

10. The method of claim 9, wherein the gemstone is a diamond having a culet and a girdle, and the surface is a pavilion lower main facet extending along a direction from the culet of the diamond to the girdle of the diamond, and
    wherein the diffraction grating has an orientation with an angle relative to the direction.

11. The method of claim 1, further comprising:
    identifying a second region on a second surface of the gemstone having an optical value higher than one or more other regions on the second surface of the gemstone by analyzing the three-dimensional model of the gemstone;
    in response to determining that the optical value of the second region on the second surface of the gemstone is no smaller than a predetermined threshold, determining a second diffractive structure to be arranged on the identified second region of the second surface of the gemstone, such that the gemstone with the diffractive structure and the second diffractive structure has a higher optical performance than without the diffractive structure and the second diffractive structure; and
    in response to determining that the optical value of the second region on the second surface of the gemstone is smaller than the predetermined threshold, determining not to arrange a diffractive structure on the second surface of the gemstone.

12. The method of claim 1, further comprising determining a second diffractive structure to be arranged on a region of a surface of a second gemstone,
wherein the second diffractive structure of the second gemstone is different from the diffractive structure of the gemstone, such that the gemstone fabricated with the determined diffractive structure is identifiable from the second gemstone fabricated with the determined second diffractive structure.

13. The method of claim 1, further comprising:
aligning the gemstone with respect to a fabrication machine; and
fabricating the determined diffractive structure on the identified region of the surface of the gemstone.

14. The method of claim 13, further comprising: taking digital photographs of the surfaces of the gemstone,
wherein aligning the gemstone comprises: mapping the digital photographs with the three-dimensional model of the gemstone, such that the identified region of the surface of the gemstone is matched with a place where the fabrication machine is to fabricate the diffractive structure.

15. The method of claim 13, further comprising:
measuring an optical performance of the gemstone with the fabricated diffractive structure on the identified region of the surface of the gemstone; and
adjusting, based on a result of the measurement, one or more parameters of the diffractive structure to enhance the optical performance of the gemstone.

16. A method of fabricating diffractive structures on a gemstone, comprising:
identifying a region on a surface of the gemstone having an optical value higher than one or more other regions on the surface of the gemstone by simulating light propagation in a digital model of the gemstone;
generating irradiance data representing light reflection distribution of the light on the surface;
determining that a total energy enclosed in the surface of the gemstone is no smaller than a predetermined threshold;
determining a diffractive structure to be arranged on the identified region of the surface of the gemstone;
aligning the gemstone with respect to a fabrication machine; and
fabricating the determined diffractive structure on the identified region of the surface of the gemstone based on information of the determined diffractive structure and the alignment of the gemstone.

17. A method of managing optical characteristics of a gemstone with diffractive structures, the method comprising:
obtaining a three-dimensional model of the gemstone including representations of a plurality of pairs of surfaces of the gemstone, each pair including two surfaces opposite to each other in a planar view of the three-dimensional model;
selecting one surface from a pair of surfaces to be arranged a diffractive structure, the other surface of the pair of surfaces being left blank without arranging a diffractive structure;
identifying a region on the selected surface having an optical value higher than one or more other regions on the selected surface by analyzing the three-dimensional model of the gemstone, wherein analyzing the three-dimensional model of the gemstone comprises:
simulating propagation of an incident light through the gemstone and reflected by the selected surface;
generating irradiance data representing light reflection distribution of the light on the selected surface;
determining that a total energy enclosed in the selected surface of the gemstone is no smaller than a predetermined threshold; and
determining a respective diffractive structure to be arranged on the identified region, such that the gemstone with the respective diffractive structure has a higher optical performance than without the diffractive structure.

18. The method of claim 17, further comprising selecting one surface from each pair of the plurality of pairs of surfaces,
wherein selecting one surface from each pair comprises selecting the surfaces from the plurality of pairs of surfaces such that the selected surfaces are evenly distributed around the gemstone.

* * * * *